(12) United States Patent
Canovas Vidal et al.

(10) Patent No.: US 10,136,805 B2
(45) Date of Patent: *Nov. 27, 2018

(54) APPARATUS, SYSTEM, AND METHOD FOR INTRAOCULAR LENS POWER CALCULATION USING A REGRESSION FORMULA INCORPORATING CORNEAL SPHERICAL ABERRATION

(71) Applicant: AMO Groningen B.V., Groningen (NL)

(72) Inventors: Carmen Canovas Vidal, Groningen (NL); Pablo Artal, Murcia (ES)

(73) Assignee: AMO Groningen B.V., Groningen (NL)

(*) Notice: Subject to any disclaimer, the term of this patent is extended or adjusted under 35 U.S.C. 154(b) by 0 days.

This patent is subject to a terminal disclaimer.

(21) Appl. No.: 15/212,640

(22) Filed: Jul. 18, 2016

(65) Prior Publication Data

US 2016/0324414 A1 Nov. 10, 2016

Related U.S. Application Data

(62) Division of application No. 14/148,420, filed on Jan. 6, 2014, now Pat. No. 9,393,108, which is a division
(Continued)

(51) Int. Cl.
*A61B 3/00* (2006.01)
*A61B 3/107* (2006.01)
*A61F 2/16* (2006.01)
*A61B 3/10* (2006.01)

(52) U.S. Cl.
CPC .............. *A61B 3/0025* (2013.01); *A61B 3/10* (2013.01); *A61B 3/107* (2013.01); *A61F 2/164* (2015.04);
(Continued)

(58) Field of Classification Search
CPC ........... A61B 3/10; A61B 3/103; A61B 3/107; A61B 3/117; A61B 3/1005; A61B 3/0025;
(Continued)

(56) References Cited

U.S. PATENT DOCUMENTS 5,777,718 A 7/1998 Kohayakawa
6,052,180 A 4/2000 Neal et al.
(Continued)

FOREIGN PATENT DOCUMENTS

| CN | 1951340 A | 4/2007 |
| WO | 2010028654 A1 | 3/2010 |
| WO | 2012024152 A1 | 2/2012 |

OTHER PUBLICATIONS

Applegate R.A., et al., "Interaction Between Aberrations to Improve or Reduce Visual Performance," Journal of Cataract and Refractive Surgery, 2003, vol. 29 (8), pp. 1487-1495.
(Continued)

*Primary Examiner* — Howie Matthews
(74) *Attorney, Agent, or Firm* — Johnson & Johnson Surgical Vision, Inc.

(57) ABSTRACT

An intraocular lens, and a system and method of providing an intraocular lens, having at least one characteristic of the intraocular lens customized in accordance with a modified regression that includes a modification for corneal spherical aberration. The lens, system and method may indicate measuring at least one biometric parameter of an eye at a desired light level, determining a desired postoperative condition of the eye, obtaining a corneal spherical aberration of the eye, applying at least one empirically derived regression calculation, and predictively estimating, in accordance with an output of the at least one empirically derived regression calculation, the at least one characteristic of the intraocular lens to obtain the desired postoperative condition. The
(Continued)

empirically derived regression calculation includes at least a product of the corneal spherical aberration with an empirically derived corneal spherical aberration constant, and a mathematical indication of the at least one biometric parameter or one of the paraxial regression formulas commonly used in clinical practice to calculate IOL power in normal patients.

8 Claims, 28 Drawing Sheets

Related U.S. Application Data of application No. 12/969,060, filed on Dec. 15, 2010, now Pat. No. 8,623,081.

(52) U.S. Cl.
CPC .......... *A61F 2/1613* (2013.01); *A61F 2/1637* (2013.01); *A61F 2240/002* (2013.01)

(58) Field of Classification Search
CPC .... A61F 2009/00878; A61F 2009/0088; A61F 2009/00882; A61F 2009/00897; A61F 9/007; A61F 2/1637; A61F 2/1613; A61F 2/164

See application file for complete search history.

(56) References Cited

U.S. PATENT DOCUMENTS

| | | | |
|---|---|---|---|
| 6,130,419 | A | 10/2000 | Neal |
| 6,609,793 | B2 | 8/2003 | Norrby et al. |
| 6,634,750 | B2 | 10/2003 | Neal et al. |
| 6,908,196 | B2 | 6/2005 | Herekar et al. |
| 7,044,604 | B1 | 5/2006 | Arrowsmith |
| 7,455,407 | B2 | 11/2008 | Neal et al. |
| 7,553,022 | B2 | 6/2009 | Neal et al. |
| 7,980,699 | B2 | 7/2011 | Neal et al. |
| 7,988,290 | B2 | 8/2011 | Campbell et al. |
| 7,988,292 | B2 | 8/2011 | Neal et al. |
| 8,126,246 | B2 | 2/2012 | Farrer et al. |
| 8,260,024 | B2 | 9/2012 | Farrer et al. |
| 2006/0030938 | A1 | 2/2006 | Altmann |
| 2007/0260157 | A1 | 11/2007 | Norrby |
| 2012/0158132 | A1 | 6/2012 | Canovas et al. |

OTHER PUBLICATIONS

Beiko G.H., et al., "Distribution of Corneal Spherical Aberration in a Comprehensive Ophthalmology Practice and Whether Keratometry can Predict Aberration Values," Journal of Cataract and Refractive Surgery, 2007, vol. 33 (5), pp. 848-858.

International Search Report and Written Opinion for Application No. PCT/US2011/064914, dated Mar. 19, 2012, 13 pages.

Wang L., et al., "Evaluation of Intraocular Lens Power Prediction Methods Using the American Society of Cataract and Refractive Surgeons Post-Keratorefractive Intraocular Lens Power Calculator," Journal of Cataract and Refractive Surgery, 2010, vol. 36 (9), pp. 1466-1473.

International Search Report and Written Opinion for Application No. PCT/US2017/027489, dated Oct. 4, 2017, 12 pages.

APPARATUS, SYSTEM, AND METHOD FOR INTRAOCULAR LENS POWER CALCULATION USING A REGRESSION FORMULA INCORPORATING CORNEAL SPHERICAL ABERRATION

This application claims priority to and is a divisional application of U.S. application Ser. No. 14/148,420, filed on Jan. 6, 2014, now U.S. Pat. No. 9,393,108 which is a divisional of U.S. application Ser. No. 12/969,060, filed on Dec. 15, 2010, now U.S. Pat. No. 8,623,081, issued on Jan. 7, 2014, the entirety of which are hereby incorporated by reference.

FIELD OF THE INVENTION

The present invention relates generally to power calculations for intraocular lenses (IOLs) and, more particularly, is directed to an apparatus, system and method to develop and use a regression formula incorporating corneal spherical aberrations in order to select a suitable power for an IOL to be implanted into an eye in order to obtain a predetermined refractive outcome.

BACKGROUND OF THE INVENTION

Intraocular Lenses (IOLs) are frequently used for restoring or improving visual performance, such as after cataract surgery. Because an IOL may be selected from various providers and in differing IOL powers, reliable systems and methods to select IOL powers to achieve the desired refractive outcome for a patient are needed. More particularly, it is most desirable to select an IOL power that will achieve emmetropia after surgery, independent of the refractive state or clinical history of the patient prior to implantation. The term emmetropia, and variations thereof, is used herein to indicate a state of vision in which an object at infinite distance from the subject eye is in sharp focus on the patient's retina.

The IOL power necessary to achieve emmetropia is often calculated using regression theory. One of the first calculations using this approach was the Saunders, Retzlaff, and Kraff formula (SRK). It is a regression formula empirically derived from clinical data to indicate the optimal power for an IOL. The SRK regression formula is:

$$P = A - 2.5 * AXL - 0.9 * K$$

where P is the IOL power, A is the lens constant, AXL is the axial length in millimeters, and K is the average corneal power in diopters. Unfortunately, the SRK regression formula may lead to the indication of a stronger IOL power for long eyes, and a weaker IOL power for short eyes. That is, the SRK typically underestimates the necessary IOL power to obtain emmetropia for short eyes, and overestimates the IOL power necessary for long eyes.

In order to remedy these shortcomings of SRK, the SRKII regression formula was developed, incorporating further empirical analysis of clinical data. In the SRKII regression, an additional constant is provided to modify the lens constant A from the SRK formula. The modification to A is based on whether the eye is long or short. More particularly, the SRKII formula is:

$$P = A - 2.5 * AXL - 0.9 * K + F$$

where F is a known constant that is equal to +3D at less than 20 millimeters of axial length (AXL), +2D at 20 to 20.9 millimeters, +1D at 21 to 21.9 millimeters, 0D at 22 to 22.5 millimeters, and −0.5D at greater than 24.5 millimeters. By way of example, if SRK yields an IOL power of +32D, SRKII may yield an IOL power of +35D (+32D+3D=+35D), if the patient's axial length is less than 20 mm.

An additional regression method, developed in an effort to address the shortcomings of SRK and SRKII, is the SRK/T formula. In the SRK/T method, the empirical calculation based on regressions is used to predict the position of the IOL in the eye after surgery. Once the position is known, the IOL power to implant is calculated by simple paraxial optics, taking into account that the eye can be modeled under this approximation as a two lens system (wherein the two lenses are the cornea and the IOL), focusing on the retina. This approach is based on Fyodorov's theoretical formula.

There are numerous formulas for calculating IOL power, such as the aforementioned, and additionally the Haigis, Olsen, and Holladay 1 and 2 models, for example. An in-depth analysis of IOL power calculation methods is provided in Shammas H J (ed.), *Intraocular Lens Power Calculations*, Thorofare, N.J.; Slack (2004), which is incorporated herein by reference as if set forth in its entirety.

However, it is well known that these formulas do not provide accurate predictions to achieve emmetropia for all preoperative refractive states. While a good prediction may be obtained using some of the aforementioned formulas to achieve emmetropia after surgery for emmetropic or close to emmetropic patients prior to surgery, errors arise for those with extreme myopia or hyperopia. These deviations for extreme eyes are not unexpected, because empirical regressions have been back calculated from "average," that is, emmetropic or near-emmetropic, eyes. Due to the regression nature of these formulas, even emmetropic eyes with a non common or odd configuration may not be well predicted, since they are not inside of the regression. Thus, it is also possible to have errors in emmetropic eyes.

For example, FIG. 1 illustrates the variations from the predicted outcome, for the same patient (labeled by patient number), provided by different regression calculation methods. As illustrated, the differences from the predicted outcome for a particular patient using the IOL power recommended by the current regression calculations become more extreme for progressively more myopic eyes (i.e., eyes having an average IOL power predicted of less than 15D) or hyperopic eyes (i.e., eyes having an average IOL power predicted of greater than 25D).

The way in which these deviations from the plano refraction are typically approached is by the optimization of the A constant. Thus, possible bias, as well as, surgical technique can be considered by personalizing this constant. This approach can remove small biases, so that the average population can have zero refraction after surgery. However, the standard deviation is not lowered, meaning that IOL power for those non average eyes is still not correctly predicted.

Postlasik eyes are a particular example of eyes that are not "average," in part because the corneal power of the post-lasik eye has been modified by lasik surgery. A factor that causes difficulty in obtaining an optimal IOL power outcome for the post-lasik eye is the corneal power (K) in the regression formulas above, which is often incorrectly measured by topographers or keratometers after a lasik procedure. Additionally, the decoupling that occurs between the anterior and posterior corneal radius after lasik makes the effective index calculated for "average" patients inaccurate for postlasik eyes. Thus, it is well known that regression formulas do not typically provide a recommended IOL power that will produce the desired refractive outcome for post-lasik patients and thus regular regression formulas cannot be directly applied to this population without modification.

Moreover, it has been widely reported that the lasik procedure may typically generate large amounts of corneal aberrations. This may be inferred because post-lasik patients typically present higher amounts of corneal aberrations, likely due to the lasik surgery, than would an "average" patient. Such aberrations should not be excluded in IOL power predictions if the desired refractive outcome is to be obtained. Currently, aberrations are not incorporated in regression formulas, which are instead based on paraxial optics as discussed above.

The importance of corneal aberrations in IOL power calculations has been demonstrated in, for example, Application 61/375,657 filed on Aug. 20, 2010 entitled "Apparatus, System and Method for an Empirically-Based, Customized Intraocular Lens Power Calculation". The ray tracing approach is based on the exact solution of Snell's law for all of the rays passing through the ocular surfaces placed in positions defined by biometric measurements. This is a personalized model, where all the patient's biometric measurements are considered, in contrast with regression formulas, which are based on averages. In this customized model, all corneal aberrations can also be introduced, thus making it applicable for both normal and postlasik patients, for example.

FIG. 2 shows the residual refraction (SE meaning spherical equivalent) achieved by different approaches including the SRK/T as well as the ray tracing approach with and without corneal aberrations for 17 normal patients. Because of the small amount of aberrations, the impact on IOL power calculation is limited.

FIG. 3 shows the improvement in IOL power prediction considering corneal aberration (custom+ab) in the ray tracing approach with respect to the current state of the art in IOL power calculation for postlasik eyes (double K) and also with the same ray tracing procedure without considering corneal wavefront aberrations for 12 patients. FIG. 4 reveals that this improvement is related to the lower standard deviation, so IOL power calculations can be more predictable and accurate when corneal aberrations are considered. FIG. 5 discloses that the improvement in the accuracy of IOL power calculations considering corneal aberrations is mainly due to spherical aberration (z12), since this parameter is highly correlated with the difference in IOL power prediction with and without considering corneal aberrations (CWA_influence).

Although ray tracing may be the most theoretically accurate way to calculate IOL power, all inputs must be very accurate, since there is not an A constant to optimize in case of errors or bias. Another disadvantage of this procedure is that is relatively slow, since the area under the radial MTF is used as an optimized parameter and the computation for this parameter takes time.

Thus, the need exists for an apparatus, system and method that provide greater accuracy in predicting optimal IOL power for particular patients using regression theory, for eyes inside and outside the "average" range.

BRIEF DESCRIPTION OF THE FIGURES

Embodiments of the present invention will be understood with reference to the detailed description in conjunction with the accompanying figures, in which like numerals indicate like aspects, and wherein.

SUMMARY OF THE INVENTION

Figure 1:
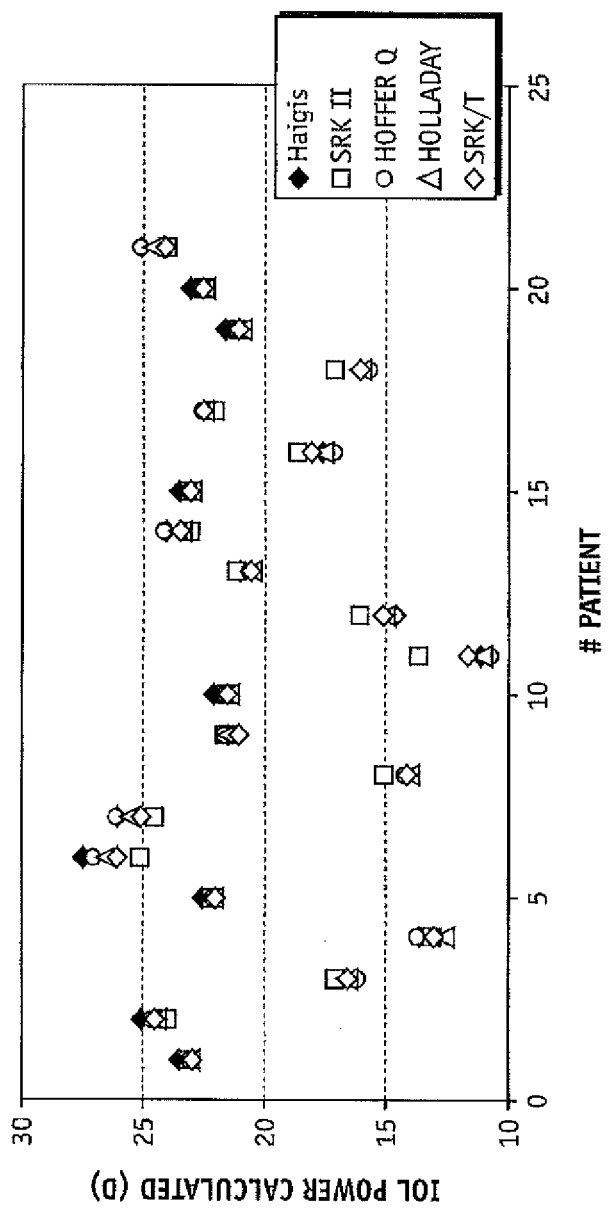
FIG. 1 is a histogram illustrating required IOL power predicted by prior art regression models for normal patient that have not undergone cataract surgery.
Figure 2:
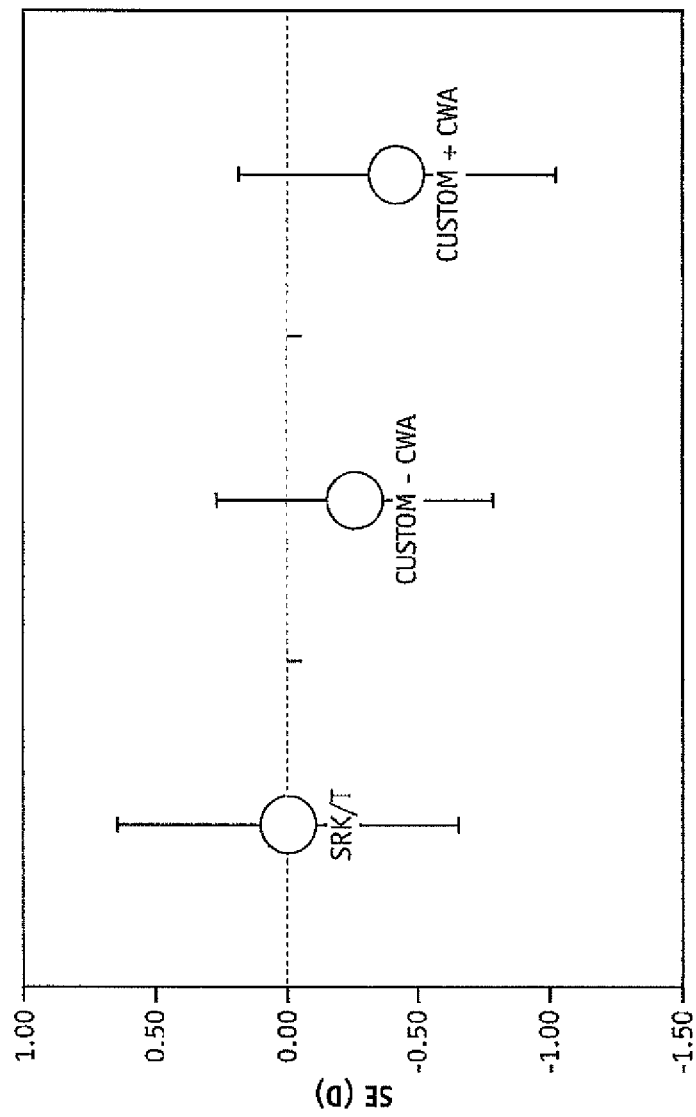
FIG. 2 is a graphical representation comparing the average residual spherical equivalent achieved with ray tracing with and without adding corneal aberrations and current paraxial formulas in 17 normal patients.
Figure 3:
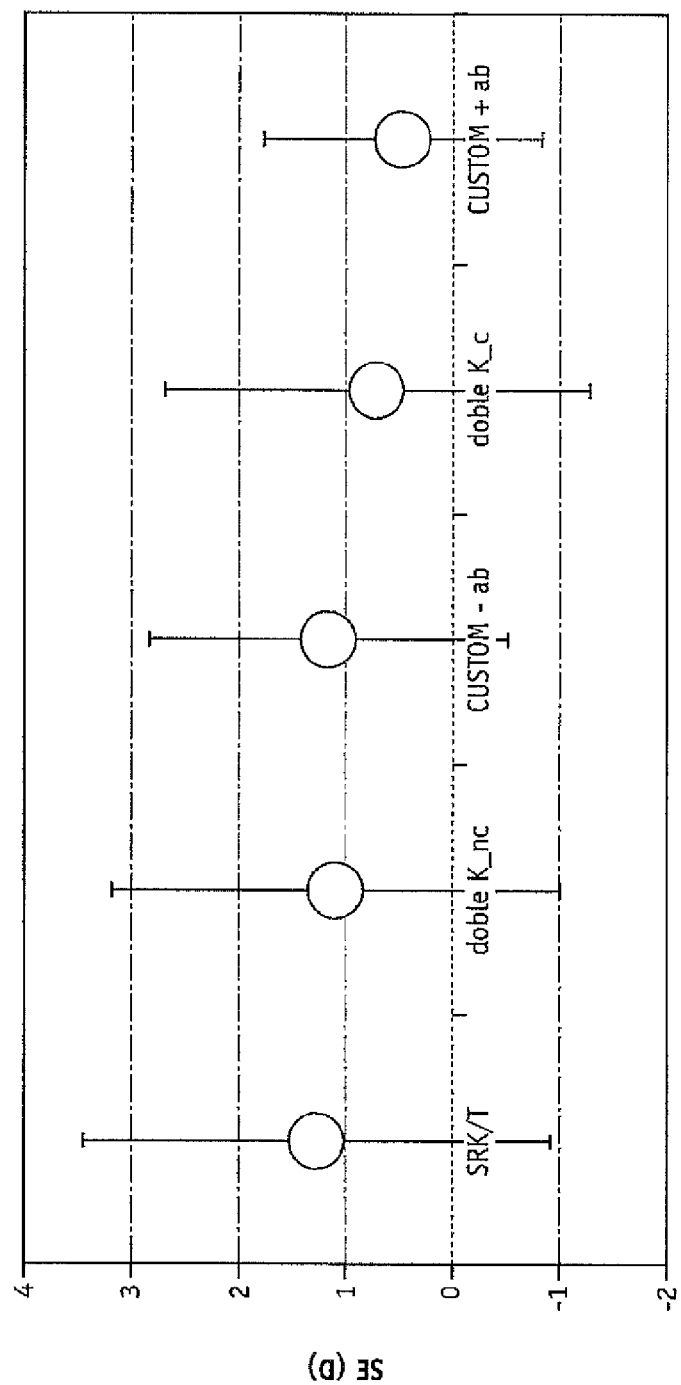
FIG. 3 is a graphical representation comparing the average residual spherical equivalent with ray tracing with and without adding corneal aberrations and current paraxial formulas in 12 postlasik patients.
Figure 4:
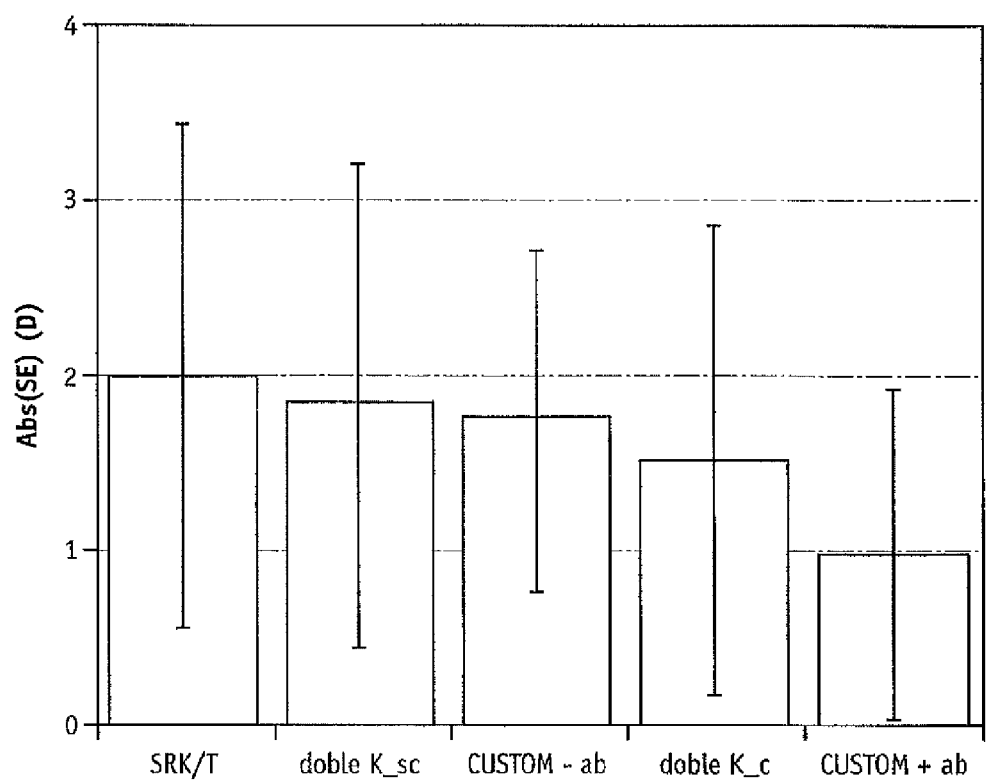
FIG. 4 is a graphical representation comparing the average absolute prediction error achieved with ray tracing with and without adding corneal aberrations and current paraxial formulas in 12 postlasik patients.
Figure 5:
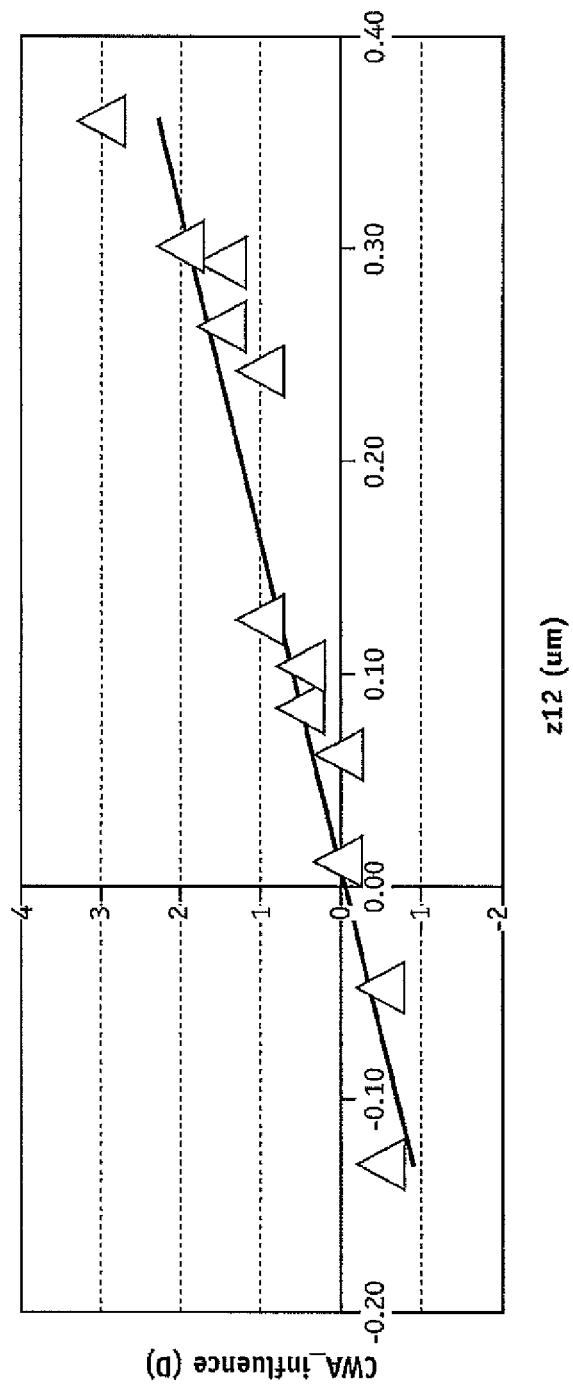
FIG. 5 is a graphical representation comparing difference between ray tracing predictions with and without considering corneal aberrations versus the amount of spherical aberration in postlasik patients.

The present invention includes an intraocular lens, and a system and method of customizing at least one characteristic of an intraocular lens, in accordance with a modified regression that includes a modification for corneal spherical aberration in the modified regression.

The method may include defining a desired postoperative condition of the eye, measuring at least one biometric parameter of an eye, obtaining a corneal spherical aberration of the eye at the desired pupil diameter, applying at least one empirically derived regression calculation, and predictively estimating, in accordance with an output of the at least one empirically derived regression calculation, the at least one characteristic of the intraocular lens to obtain the desired postoperative condition. The empirically derived regression calculation includes at least a product of the corneal spherical aberration with an empirically derived corneal spherical aberration constant, and a mathematical indication of the at least one biometric parameter.

The desired postoperative condition may comprise a postoperative refraction, or the at least one characteristic of the intraocular lens may be an optical power, for example. The at least one biometric parameter may be at least one of axial length, anterior chamber depth and corneal power.

The empirically derived regression calculation may further include a classical regression formula, comprised of the mathematical indication of the at least one biometric parameter, and at least a second constant that is at least one of arithmetically and multiplicatively applied to the classical regression formula. The method may further include selecting an intraocular lens for implantation in accordance with the output of the empirically derived regression calculation.

In addition to aspects of the method of the present invention, the system of the present invention may include a first computing device capable of measuring at least one biometric parameter of an eye, a second computing device capable of measuring and processing or introducing corneal spherical aberration of the eye at different pupil diameters, and a third computing device capable of applying, by at least one computing processor, a modified regression to the at least one biometric parameter and the corneal spherical aberration to output an optimized one of the optical power to obtain a desired postoperative condition. In exemplary embodiments, one of the forms of the modified regression is:

$$P=A*\text{Formula}+D*(\text{corneal spherical aberration})+E$$

where the constant D is an empirically derived factor across a population of eyes, E is another constant empirically derived result from the regression procedure, and wherein the Formula is a classical regression formula.

The system may further include a feedback input to the third computing device for modifying the modified regression in accordance with the optimized optical power for patients that have already undergone cataract surgery. The Formula may be one selected from Hoffer Q regression, Haigis regression, Holladay1 regression and SRK/T regression.

In addition to the aspects of the method and system of the present invention, an intraocular lens according to the present invention may include a selected optic from a plurality of available optics, wherein the selected optic may be selected based on an optical power that obeys the equation:

$$P=A*\text{Formula}+D*(\text{corneal spherical aberration})+E,$$

and the lens may further include at least one haptic for physically supporting the selected optic in situ.

Therefore, the present invention provides an apparatus, system and method that provides greater accuracy in predicting optimal IOL power for patients, and in particular, for eyes inside and outside the "average" range.

DETAILED DESCRIPTION OF THE EMBODIMENTS

It is to be understood that the figures and descriptions of the present invention have been simplified to illustrate elements that are relevant for a clear understanding of the present invention, while eliminating, for the purpose of clarity and brevity, many other elements found in typical implantable optic apparatuses, systems and methods. Those of ordinary skill in the art may thus recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to the disclosed elements and methods known to those skilled in the art.

The present invention is directed to apparatuses, systems and methods for selecting power for spherical and aspheric intraocular lenses (IOLs) to provide a predetermined refractive outcome for "average" and non-average patients. Aspects of the invention may be understood with reference to FIG. 6, which is a graphical representation of a model eye 20 having cornea 22, iris 24, retina 26, and optical axis 28. IOL 30 is disposed within eye 20, and IOL 30 may include an optic 32 and one or more haptics 34 having distal ends 38. In general, eye 20 may have the dimensional parameters illustrated by the geometry shown, including the axial length (AXL) and the anterior chamber depth (ACD) of eye 20. Other dimensional parameters that may be included in model eye 20, but that are not shown in FIG. 6, include, but are not limited to, the corneal radius (CR), the corneal power (K) and the crystalline lens thickness (LT). Model eye 20 may also include various other parameters, such as, for example, the refractive indices of the various portions of eye 20 and/or IOL 30.

In certain embodiments, distal ends 38 of haptics 34 may be disposed within a plane, defined as the lens haptic plane (LHP). In various embodiments, model eye 20 may include other information indicated by IOL 30, such as, for example, an effective principal plane of optic 32 and/or the location of optic 32 within eye 20.

Figure 6:
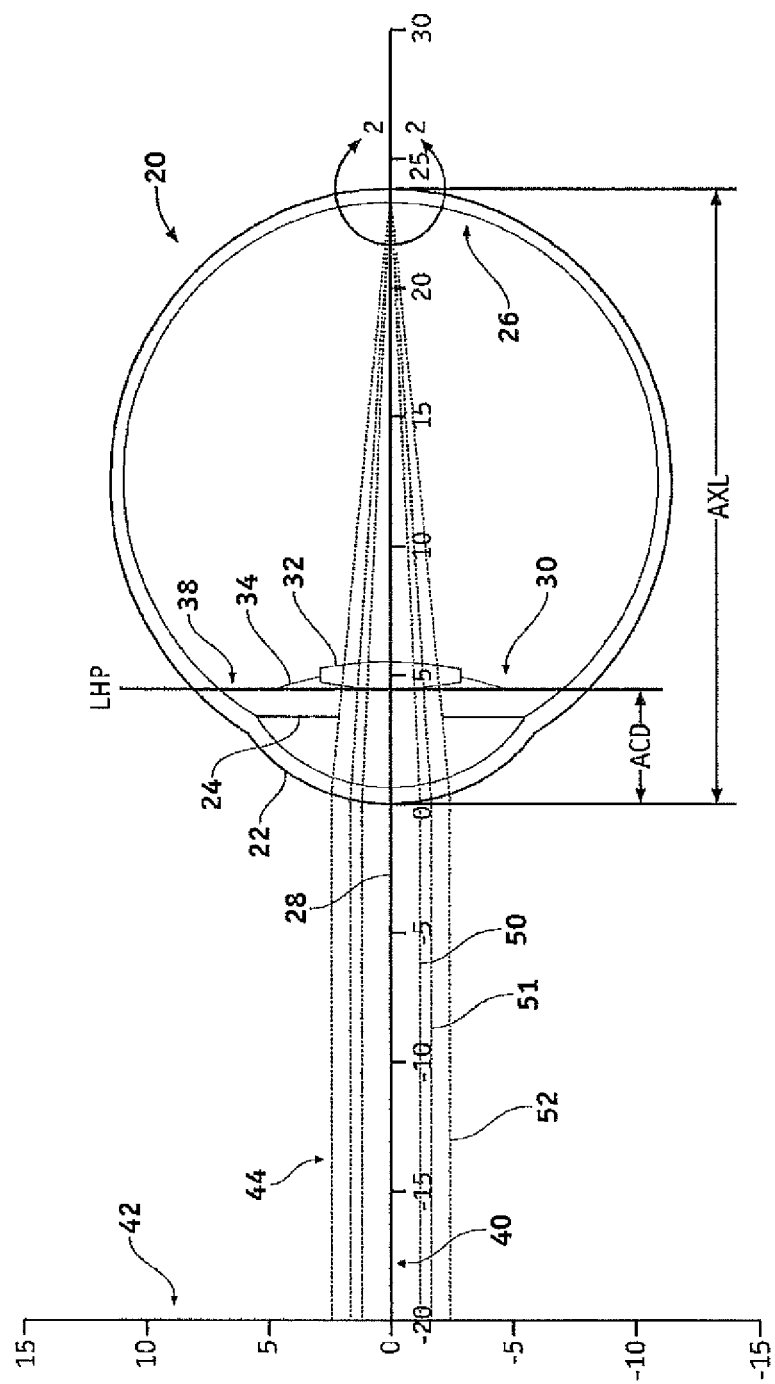
FIG. 6 is a graphical representation of the elements of an eye model used in various embodiments of the present invention.

The illustration of FIG. 6 also indicates a coordinate system having a horizontal axis 40 and a vertical axis 42, shown in units of millimeters. FIG. 6 shows a plurality of rays 44 entering cornea 22 and IOL 30. The plurality of rays 44 comprises a paraxial ray 50 that is disposed near the optical axis 28, and a marginal ray 52 that is disposed near the edge of the opening formed by the iris 24. The plurality of rays 44 additionally comprise of an averaged ray 51 disposed between the paraxial ray 50 and the marginal ray 52, for example, at a height, at the pupil, of 1/{square root over (2)} or ½ times the height of the entrance pupil height. In some embodiments, the eye model may additionally include information regarding an object or source represented by the plurality of rays 44 entering eye 20, such as, for example, the distance of the source or object from eye 20 and/or the extent of the source or object in units of length.

Figure 7:
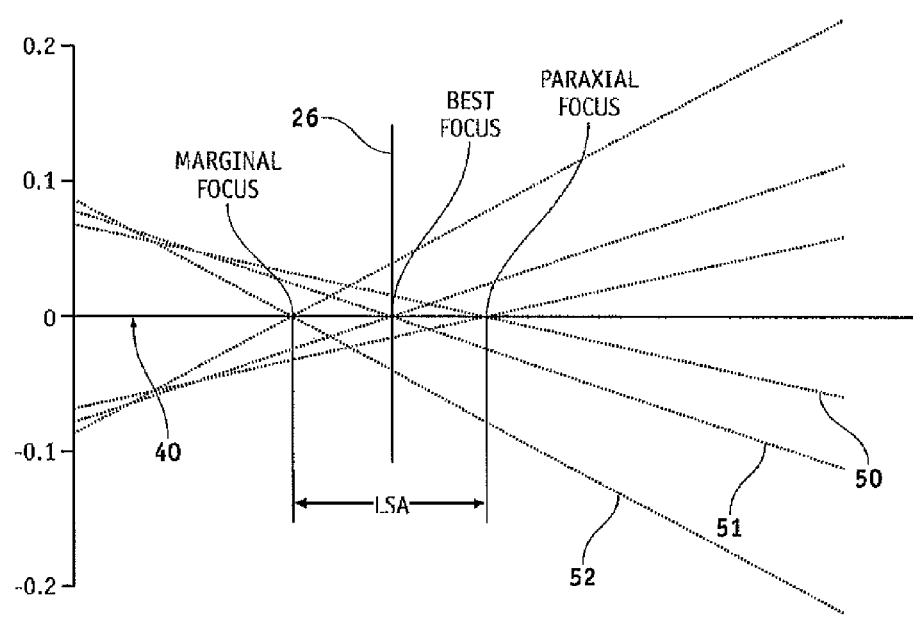
FIG. 7 is a magnified view of the retinal region of the graphical representation shown in FIG. 6.

Referring now to FIG. 7, shown is a magnified view of the region around retina 28, illustrating that rays 50, 51, 52 may come to focus at different points along optical axis 28. These points of focus are labeled as marginal focus, best focus, and paraxial focus. As illustrated, the distance between the marginal focus and the best focus may be used to define a longitudinal spherical aberration (LSA). A LSA may result, for example, when the surfaces of IOL 30 are spherical. Alternatively, one or more of the surfaces of IOL 30 may comprise an aspheric profile that is configured to reduce or eliminate spherical aberrations produced by IOL 30 or by portions of eye 20, such as corneal spherical aberrations (SA) produced by cornea 22.

The present invention may be used to select the characteristics of IOL 30 to be implanted into a subject eye or a class of subject eyes. For example, a class of subject eyes may include subjects of a particular age group or condition (e.g., a class of subjects who have had lasik or a similar procedure). In certain embodiments, measurements from a subject eye, such as the AXL, ACD, CR and/or LT, may be used in conjunction with statistical data and/or an analytical tool to determine the characteristics of IOL 30. The characteristics of the IOL resulting from embodiments of the invention are most particularly the power of the IOL, but may additionally include the thickness of the IOL, the asphericity of the IOL, and/or the location of the IOL within the eye.

The present invention also provides a customizable procedure for predicting the optimum IOL power of a specific IOL 30 for the eye of a particular individual. The apparatus, system and method discussed herein, in formulating the IOL power prediction, take into account biometric parameters of the individual patient and the corneal spherical aberration (SA) of the subject eye. The empirical data discussed herein illustrates that the apparatus, system and method are robust for average patients, as well as for patients having most levels of corneal aberration, including aberrations found in post-lasik patients.

Figure 8:
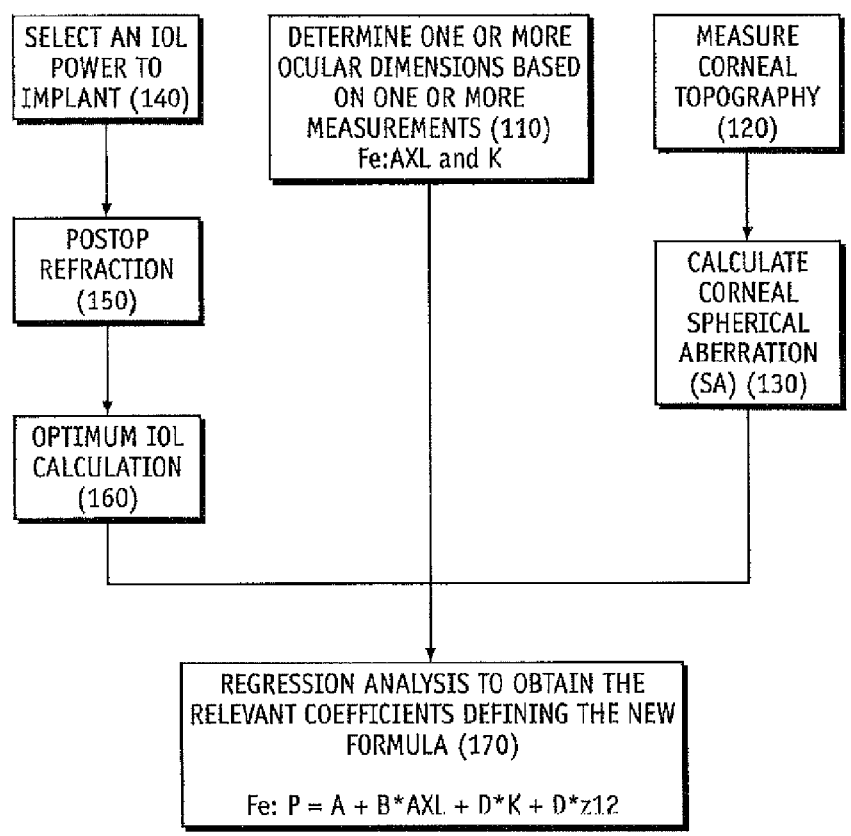
FIG. 8 is a flow chart illustrating a method to develop a regression formula to select an IOL according to exemplary embodiments of the invention.
Figure 9:
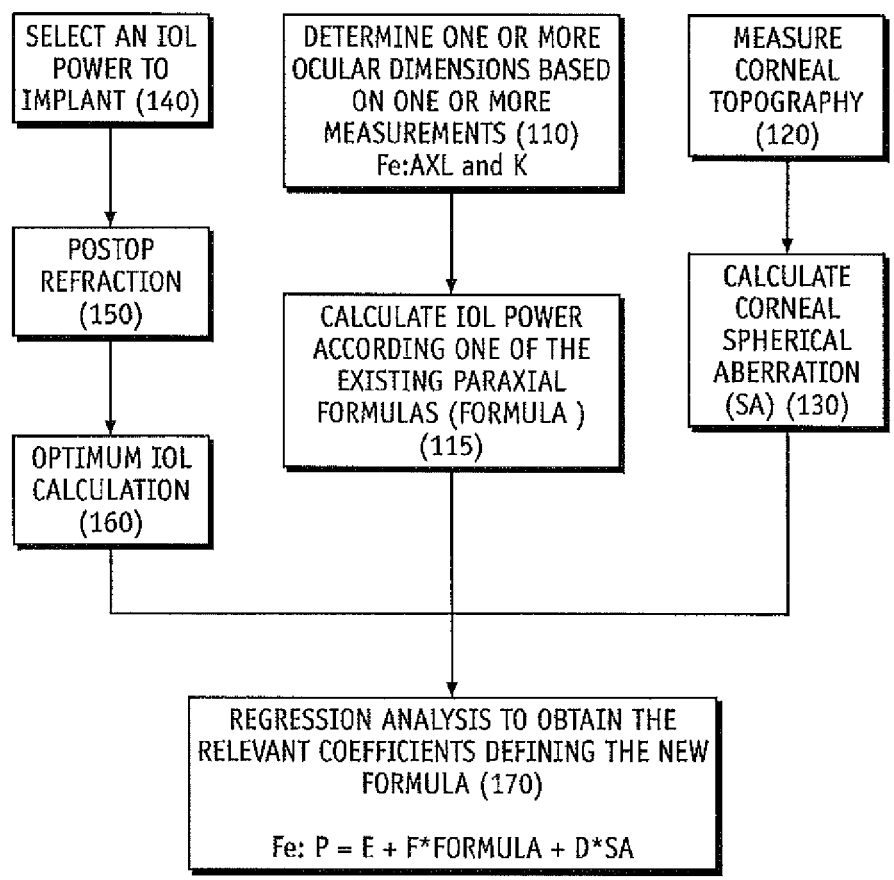
FIG. 9 is a flow chart illustrating an alternative to develop a regression formula to select an IOL using one of the existing paraxial formulas according to exemplary embodiments of the invention.

More particularly, and in accordance with FIGS. 8 and 9, exemplary methods 100/101 of selecting of an IOL may include determining the biometric parameters of the eye, such as the AXL, ACD or K, at step 110.

These two methods 100 and 101 can be used to determine a desired postoperative condition, such as a postoperative refraction and/or spherical aberration. The desired refractive outcome may be, for example, improved distance vision and/or near vision, such as providing the subject sufficient visual acuity to eliminate the need for corrective spectacles or contact lenses for near and/or distant vision. Alternatively, the refractive outcome may be to provide sufficient visual acuity such that normal vision is provided without the use of corrective external lenses, or by the use of corrective spectacles or contact lenses having a correction of less than about 3 diopters, preferably less than about 2 diopters, or more preferably less than about 1 diopter. Most particularly, the present invention has, as a desired refractive outcome, to obtain the desired postoperative outcome with the predicted IOL power.

Both methods 100 and 101 further include at step 130, a representation of the corneal topography obtained at step 120, in the form of at least one corneal aberration. These corneal aberrations can be obtained by the internal process of the apparatus used or by the external process from corneal elevations achieved by corneal topographers. It may also be obtained using an analytical tool, such as using established ray tracing procedures. As used herein, a ray tracing procedure is a procedure that simulates the light propagation and refraction, by means of an exact solution of Snell's law, for all rays passing through an optical system. Those skilled in the art will appreciate that, for example, a Zemax optical design software simulation may be employed in order to provide the ray tracing modeling discussed herein.

In accordance with step 130, the SA may be obtained pursuant to the light level, such as at the 4 mm pupil. The desired light level may simulate, for example, mesopic light (dusk). The pupil size at dusk is typically about 4 mm, but may vary between at least about 2 mm to about 6 mm or more. The mesopic light pupil size may be selected, by way of example, in part because the about 4 mm pupil is a realistic pupil for cataract patients and allows for the introduction of aberrations that are omitted in paraxial optics (herein defined as the study of optics related to small angles, and small apertures).

From these results, at step 140 the IOL power to implant for the patient will be calculated following the standard procedures in cataract surgery. At step 160 the optimum IOL power is back calculated from each patient from knowledge of the postoperative refraction, obtained at step 150. Once this is calculated in the IOL plane, this will be added to the implanted IOL power thus defining the optimum IOL power for the patient.

Using the data gained at step 160, a multiple regression analysis may be performed across several subjects in order to establish the final formula to use, based on pre-operative data and corneal spherical aberration, to predict the optimum IOL characteristics, such as the optimum IOL power, at step 170.

The main difference between method 100 (FIG. 8) and 101 (FIG. 9) is the nature of the regression data. In method 100, optimization is based directly on the constants, which weight each of the input parameters obtained at step 110, as well as the corneal spherical aberration at step 130. On the other hand, corneal spherical aberration is also considered as a parameter in method 101. In method 101, the other parameter is the IOL power calculated using preoperative data from one of the current paraxial optic formulas calculated at step 115.

In both methods, the final regression allows for improved prediction of IOL characteristics, such as IOL power, for subsequent average and non-average subjects at step 170. Because of the regression nature of these formulas, they can be continuously updated by the addition of new patients, personalizing in this way the different constants involved in the calculation.

Figure 10:
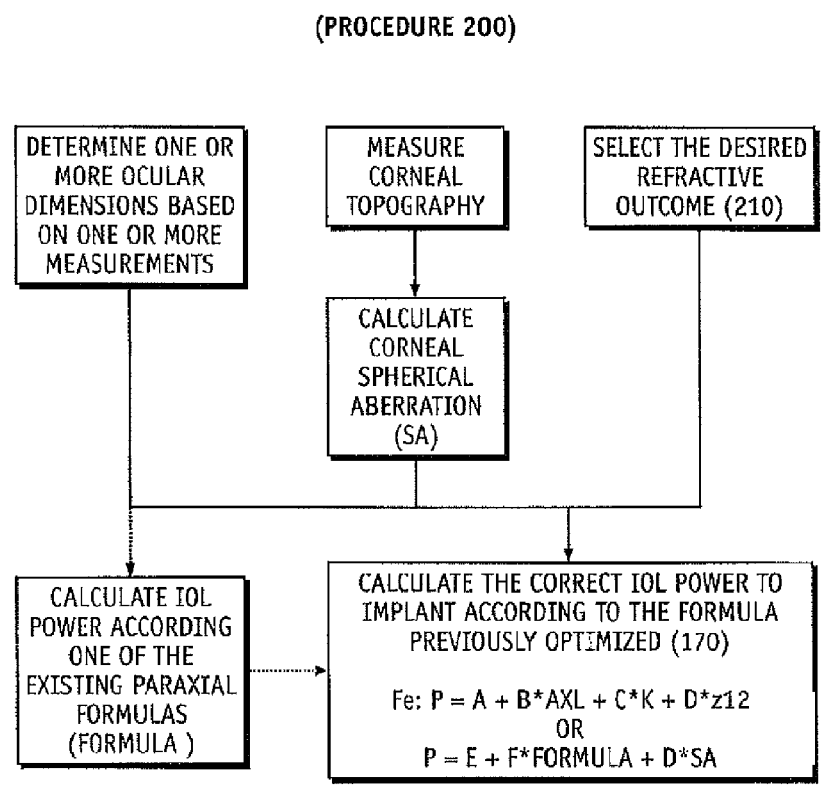
FIG. 10 is a flow chart illustrating a method of selecting an IOL according to exemplary embodiments of the invention.

Once the formula has been established, the procedure 200, described in FIG. 10, can be used to predict a desired postoperative condition in a different population than that from which formula 170 had been obtained, such as a postoperative refraction and/or spherical aberration, at step 210 by previous knowledge of biometric parameters included in the formula (directly as inputs if method 100 is applied to develop procedure 200 or, in the case of method 101, the input will be from one of the current paraxial formulas used to compute the IOL power) as well as corneal spherical aberration and the selected refractive stage after the surgery.

Methods of predicting refractive outcomes, such as refractive outcomes correcting "average" or "normal" SA in a patient group, based on IOL characteristics is well understood, and embodiments of such analyses are detailed in, for example, U.S. Pat. No. 6,609,793, which is herein incorporated by reference. More particularly, corneas of the normal population, which have historically been the subject of regression analysis at step 170, show on average positive spherical aberration. However, methods 100 or 101 of the present invention, which use a customized regression from step 170, allow for optimal IOL characteristic prediction for IOLs to treat corneas having all types of corneal SA including providing optimal IOL characteristic prediction for all types of spherical or aspheric IOLs. For example, patients who had lasik to correct myopia may have an increased value of positive spherical aberration with respect to the average normal population, while those who had corneal refractive surgery to correct hyperopia may present minor spherical aberration as compared to the average. Methods 100 or 101 provide optimal IOL characteristics, such as optimal IOL power, based on the customized regression from step 170.

The interaction between defocus, related to IOL power and spherical aberration has been reported (Applegate R. A., Marsack J. D., Ramos R., Edwin E. J. Sarver, 'Interaction between aberrations to improve or reduce visual performance', *J Cataract Refract Surg* 2003; 29:1487-1495). Thus, modifying IOL power in accordance with spherical aberration can improve visual performance. The inclusion in the regression of an additional constant, herein referred to as constant D, obtained in the regression of step 170 accounts for the variation of corneal SA parameter for individuals.

In addition, it has been clinically shown, based on a statistically significant population, that there is a nominal change of 0.7 diopters or more in the A constant in the SRK/T regression analysis as between a spherical IOL having a positive spherical aberration, and an aspherical IOL having a negative spherical aberration. Because the characteristics of the exemplary IOLs were the same in each case, with the exception of the spherical aberration (SA) parameter, it may be inferred from these clinical findings that the change in the A constant for a regression analysis is due to the SA.

The cornea may present SA in different amounts. Thus, for example, the optimal IOL power calculated by the regression from step 170 may comprise constant D to minimize the spherical equivalent (SE) of the eye. Minimization of the SE is particularly applicable in patients with less than about 1 diopter of corneal astigmatism, where visual performance is still good without the need of a toric IOL. This is an advantageous modeling approach, in part because the SE does not appreciably change due to, for example, the incision in a cataract surgery. On the contrary, corneal astigmatism and power may change pursuant to cataract surgery.

This procedure can be also extended to toric IOL power calculations. The spherical equivalent of an IOL can be calculated following a similar procedure as 200. The toric IOL power may then be obtained by the difference between the paraxial calculation for the flat and steep meridian. Further optimization may be possible considering corneal spherical aberration or other corneal aberrations in those meridians to improve the cylinder prediction as well as the spherical equivalent prediction.

Methods 100 or 101 thus account for the non-constant nature of SA in a broader population of surgical subjects, based on the applicability of methods 100 or 101 to "average" eyes, as that term is defined above, and to non-average eyes, such as eyes having significant SA. For a more detailed discussion of the variation of SA across a broad candidate population, see G. H. H. Beiko, et al., "Distribution of Corneal Spherical Aberration in a Comprehensive Ophthalmology Practice, and Whether Keratometry Can Predict Aberration Values," *J. Cataract Refract. Surg.*, vol. 33 (2007), pp. 848-858.

More particularly, the present invention improves the prediction of IOL characteristics, and specifically IOL power, across the broad population that includes average and non-average eyes through the application, at step 170 of method 100 or 101. The final regression from step 170 improves predictive accuracy by introducing an additional regression parameter, namely constant D, to account for SA. More particularly, the modification to known regression approaches may be made to improve predictive accuracy, particularly in non-average subjects, as seen in the following example of method 101:

$$P = \text{Formula} + D*SA \qquad \text{[EQUATION 1]}$$

where P is IOL power, and Formula is a regression formula known in the current art.

The customized regression from step 170, as illustrated in EQUATION 1, includes a constant obtained empirically for association with the customized variable for corneal SA. By way of example, the present inventors have empirically obtained a variety of constants D for inclusion in different ones of the classical regression formulae, and exemplary ones of these constants D are discussed further below in EQUATIONS 4-8.

Of course, those skilled in the pertinent arts will appreciate, in light of the discussion herein, that an adjustment constant or constants may also be applied to the Formula prior to or in conjunction with the modification made to account for the SA. That is, the present invention may calculate the recommended IOL power as disclosed in the following example of method 101:

$$P = E + F*\text{Formula} + D*SA \qquad \text{[EQUATION 2]}$$

where E may be zero or non-zero, and where F is non-zero.

As was described in method 100, another possible implementation of this idea is to consider the classical SRK regression model and then adjust all the constants involved in addition to those related to SA as follows:

$$P = A - B*AXL - C*K + D*SA \quad \text{[EQUATION 3]}$$

where D is the aforementioned constant applied to the SA, and A, B and C are the remaining constants which may also be optimized in order to improve the IOL power prediction.

In order to show the feasibility of taking into account, for example, the z12 Zernike term (SA) in IOL power calculations and the implementation of the invention disclosed herein, the present inventors have empirically derived a SA adjustment from a sampling of 97 average subjects using modifications to the SRK following method 100 (SRK optimized+z12) and SRK/T regressions (SRK/T modified+z12), following method 101, being the SRK/T uses a paraxial formula, and have empirically derived a SA adjustment from a sampling of 29 non-average, postlasik subjects using modifications to the SRK following method 100 (SRK optimized+z12) and for the SRK/T, Haigis, Holladay 1 and Hoffer Q formulae according method 101 (referred to be SRK/T+z12, Haigis+z12, Holladay 1+z12 and Hoffer Q+z12 respectively). Of course, those skilled in the art will appreciate that any known regression may be modified, in accordance with the present invention, using empirical data gained from any statistically significant number of subjects, and thus the present invention is not limited to the regressions and subjects or numbers of patients discussed with particularity herein.

Figure 11:
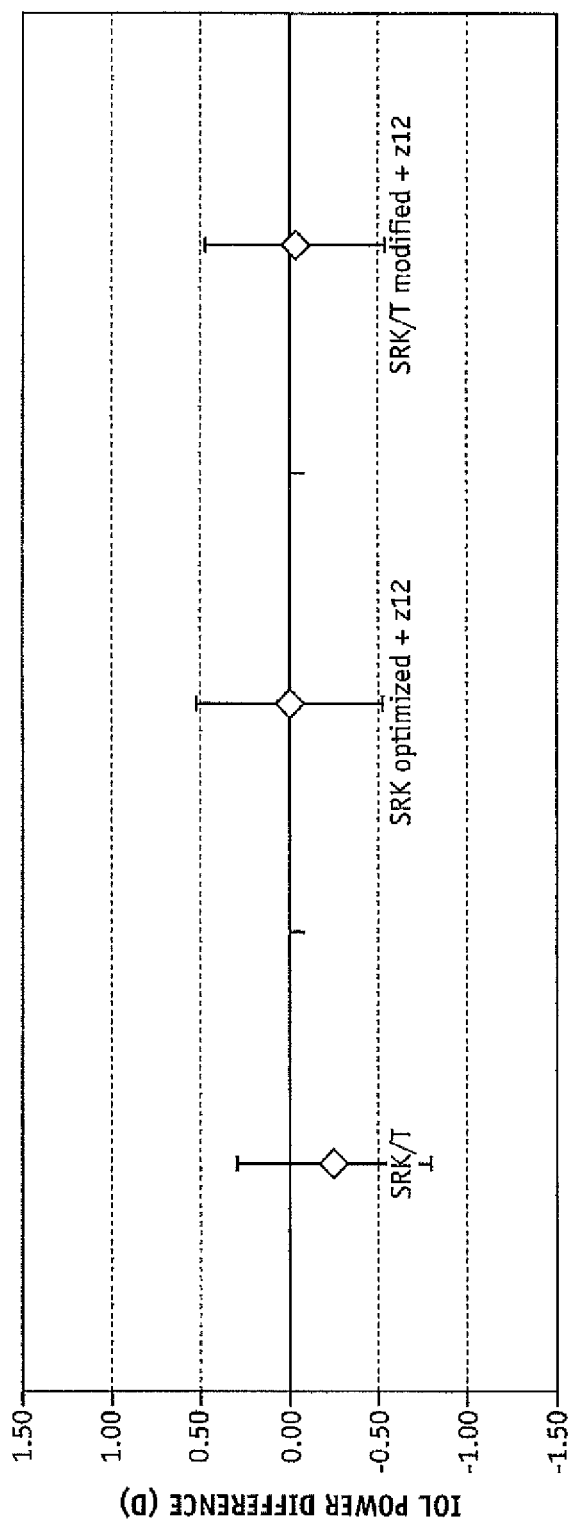
FIG. 11 is a graph comparing the residual error in IOL power calculation between the current state of art and these formulas developed used the method present here for normal patients.
Figure 12:
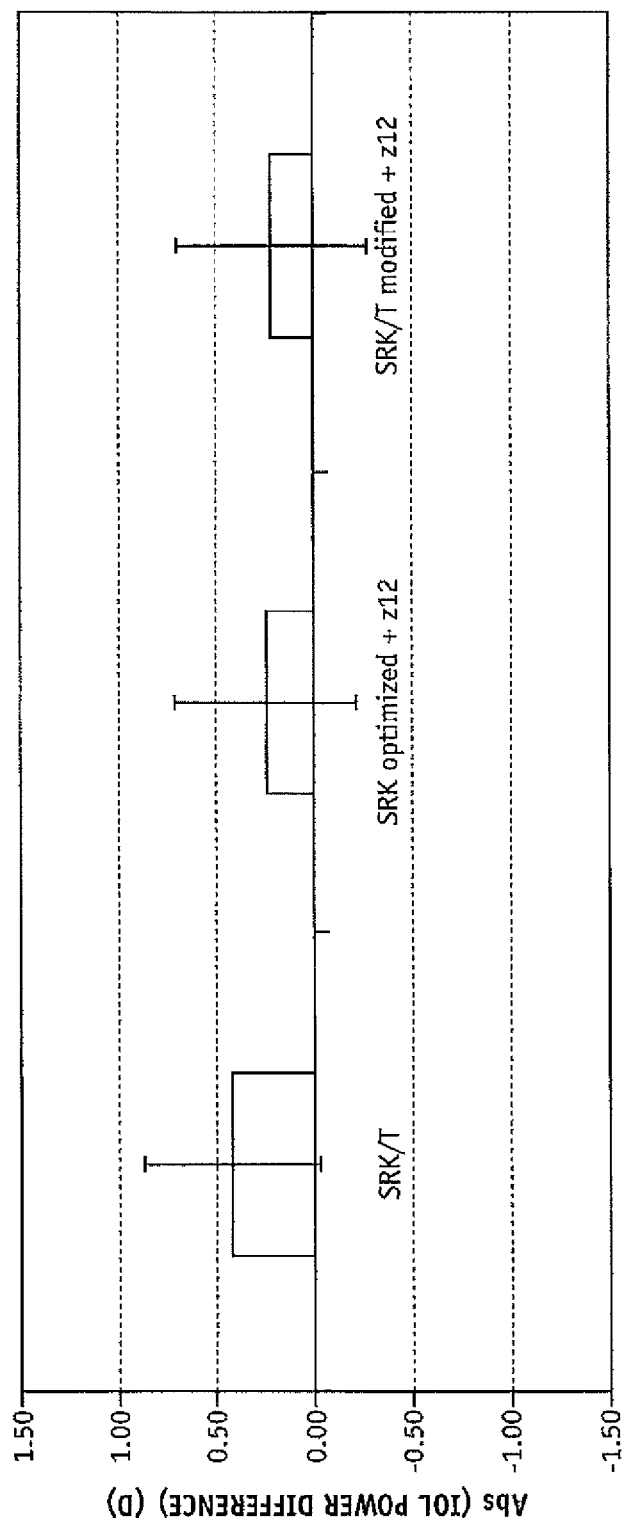
FIG. 12 is a graph comparing the absolute residual error in IOL power calculation between the current state of art and these formulas developed used the method present here for normal patients.
Figure 13:
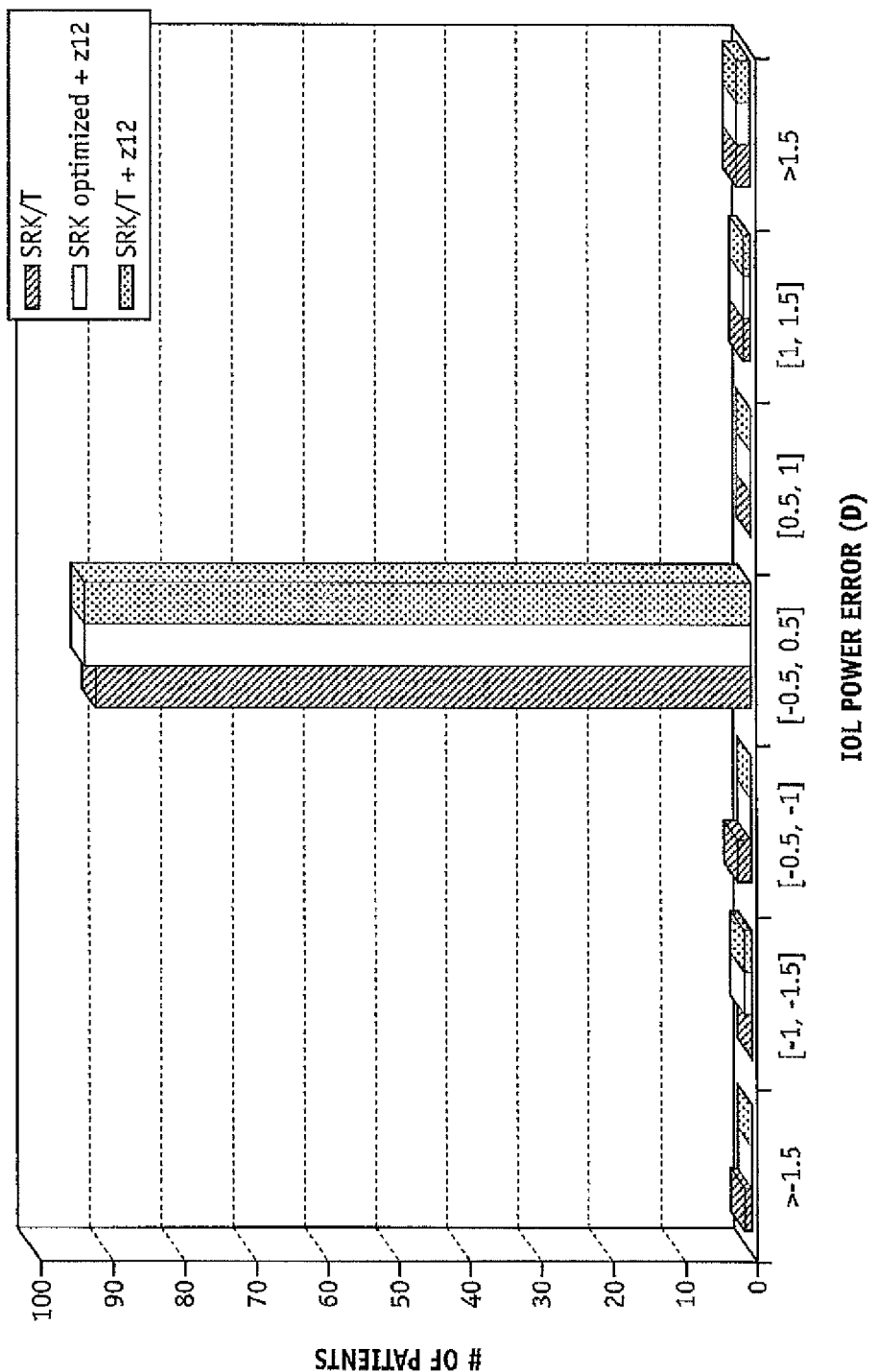
FIG. 13 shows the number of normal patients whose prediction error using different approaches is inside of different ranges.

More specifically, FIGS. 11 and 12 illustrate the comparison between the difference with respect to optimum IOL power and those calculated for the data obtained from the 97 average patients referenced above, using the SRK/T+z12 formula and the SRK optimized+z12 formula. In the illustration, the optimum IOL power was known for each patient following implantation, and was compared to the predicted outcome of the SRK/T+z12 formula and/or the SRK optimized+z12 formula (with SA in the OSA convention and at about 4 mm pupil). FIGS. 11 and 12 show a slight improvement in the error, in Diopters, in the IOL power predicted both by the SRK/T+z12 or SRK optimized+z12 formula as compared to the SRK/T formula, for patients having SA in the "average" range. FIG. 13 illustrates this slight predictive improvement in the error for the prediction using both the SRK/T+z12 or SRK optimized+z12 formula as compared to the classical SRK/T approach.

For non-average subjects, it is well known that the same formulas as used for normal patients do not provide good results. Varying solutions to improve the calculations for these types of patients have been proposed. These solutions include: calculating the IOL power based on the corneal power prior to, for example, lasik surgery; applying the "Double K" method; and the aforementioned and other retrospective regression analyses.

Various studies have shown that, of the aforementioned solutions, those based on pre-lasik data are less accurate than regression methods correcting corneal power (see, e.g. Wang L, Hill W E, Koch D D, 'Evaluation of intraocular lens power prediction methods using the American Society of Cataract and Refractive Surgeons Post-Keratorefractive Intraocular Lens Power Calculator', *J Cataract Refract Surg.* 2010 September; 36(9):1466-73, which is incorporated herein by reference as if set forth in its entirety). Thus, method 101 of the present invention, using the data related to the 29 myopic postlasik patients referenced above (including the IOL power necessary for an emmetropic outcome and the SA, as calculated from measured corneal topography, with no corneal power corrections and using no pre-lasik data), was applied to calculate the IOL power, including at step 115 the SRK/T, Hoffer Q, Holladay 1, and Haigis formulas, which results were used in addition to corneal spherical aberration to generate the corresponding modified regression formulas at step 170. In addition, method 100 was applied in the same subjects in order to develop a SRK optimized+z12 regression.

Figure 14:
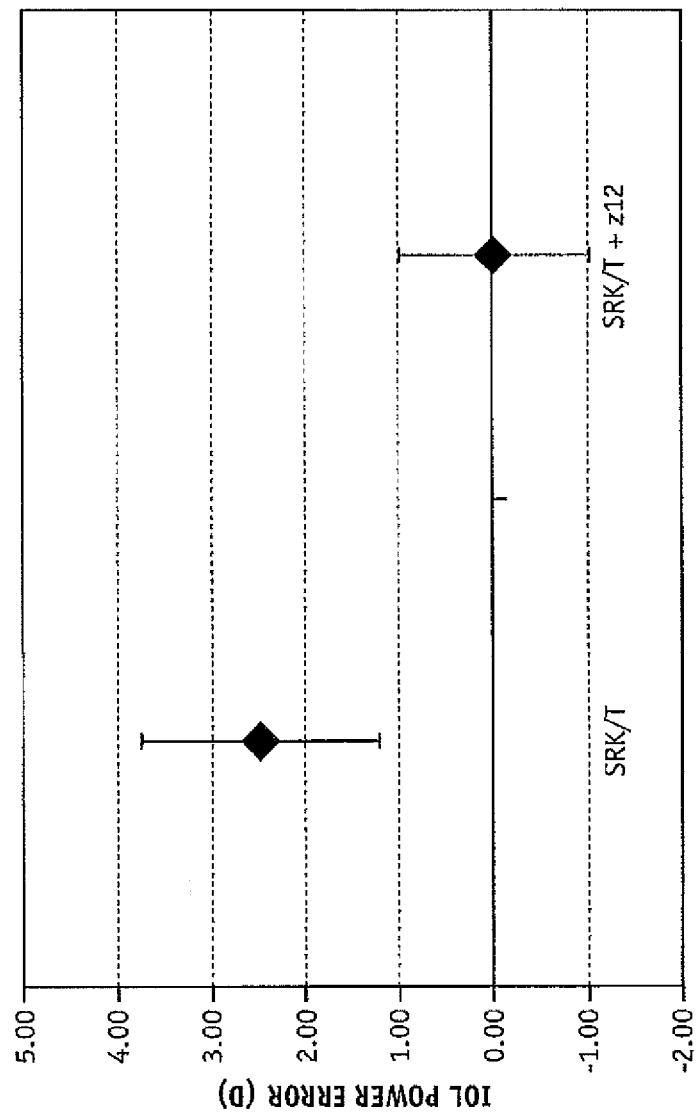
FIG. 14 shows the IOL power prediction error both for the SRK/T formula and the SRK/T considering corneal spherical aberration for postlasik patients.
Figure 15:
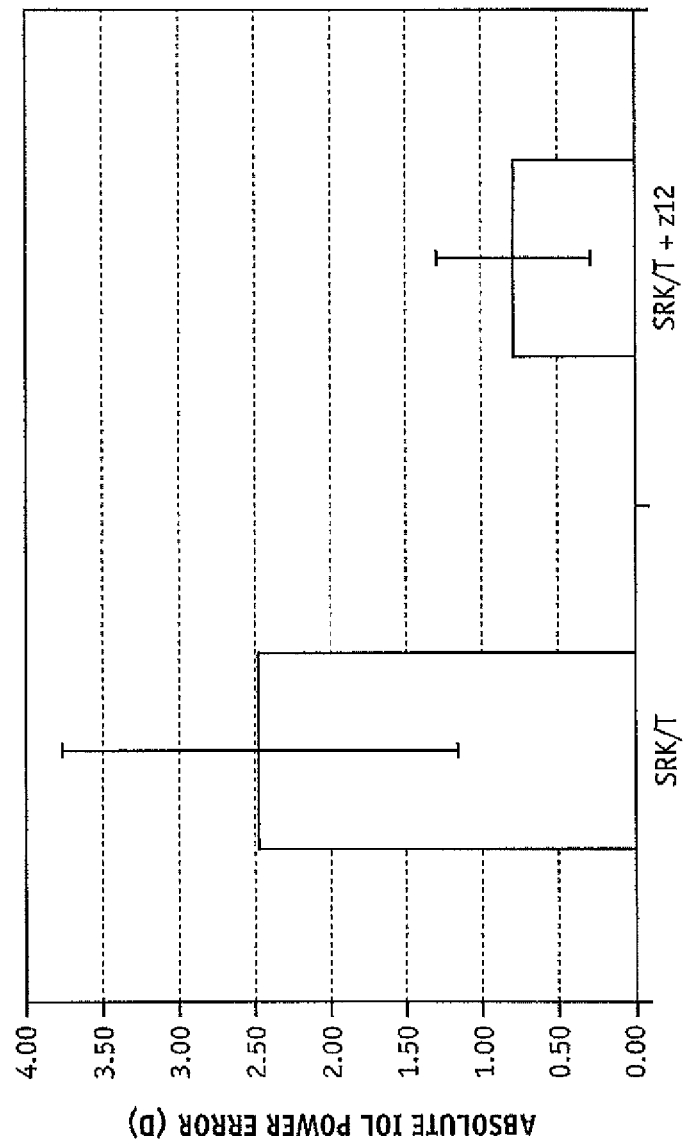
FIG. 15 shows the absolute IOL power prediction error both for the SRK/T formula and the SRK/T considering corneal spherical aberration for postlasik patients.

For example, FIGS. 14 and 15 illustrate a comparison of the error of the predicted IOL power, for the referenced 29 non-average patients, for the SRK/T and SRK/T+z12 formulae. As shown, the inclusion of the adjustment for the SA decreases the error in the predicted IOL power. More particularly, the SRK/T+z12 formula indicated at step 170 of method 101 is:

$$P = 1.70056 + 0.955562*SRK/T + 9.804702*z12. \quad \text{[EQUATION 4]}$$

Figure 16:
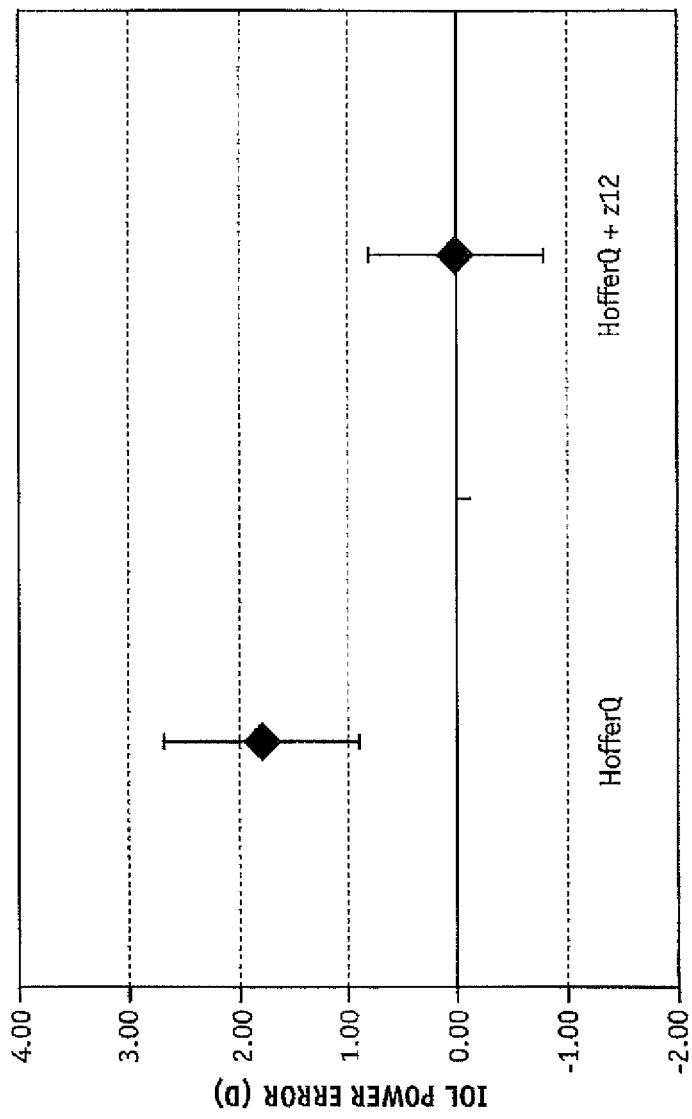
FIG. 16 shows the IOL power prediction error both for the HofferQ formula and the HofferQ considering corneal spherical aberration for postlasik patients.
Figure 17:
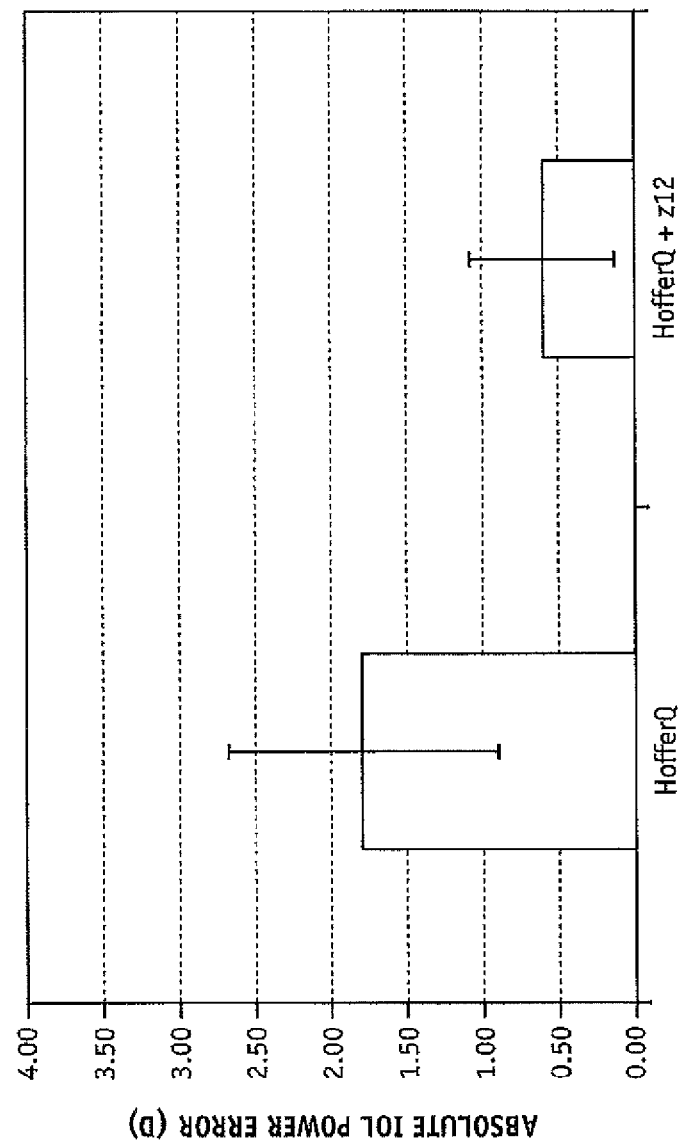
FIG. 17 shows the absolute IOL power prediction error both for the HofferQ formula and the HofferQ considering corneal spherical aberration for postlasik patients.

Further, for example, FIGS. 16 and 17 illustrate a comparison of the error of the predicted IOL power, for the referenced 29 non-average patients, for the Hoffer Q and Hoffer Q+z12 formulae. As shown, the inclusion of the adjustment for the SA substantially decreases the error in the predicted IOL power. More particularly, the Hoffer Q+z12 formula indicated at step 170 of method 101 is:

$$P = 2.057938 + 0.944393*HofferQ + 4.671033*z12. \quad \text{[EQUATION 5]}$$

Figure 18:
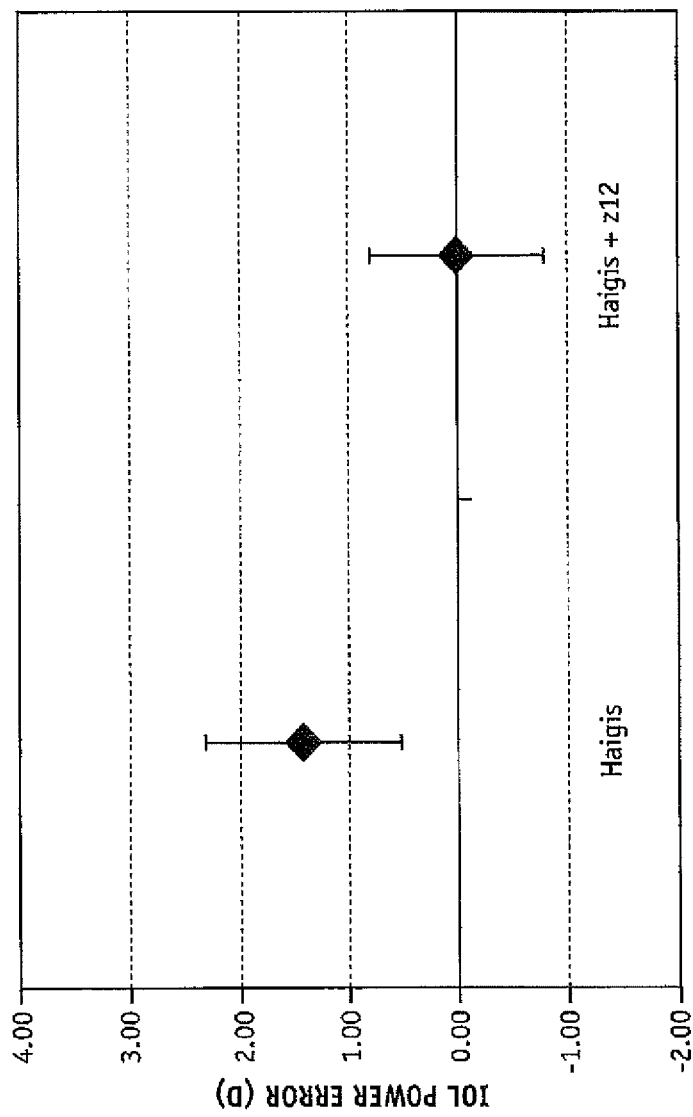
FIG. 18 shows the IOL power prediction error both for the Haigis formula and the Haigis considering corneal spherical aberration for postlasik patients.
Figure 19:
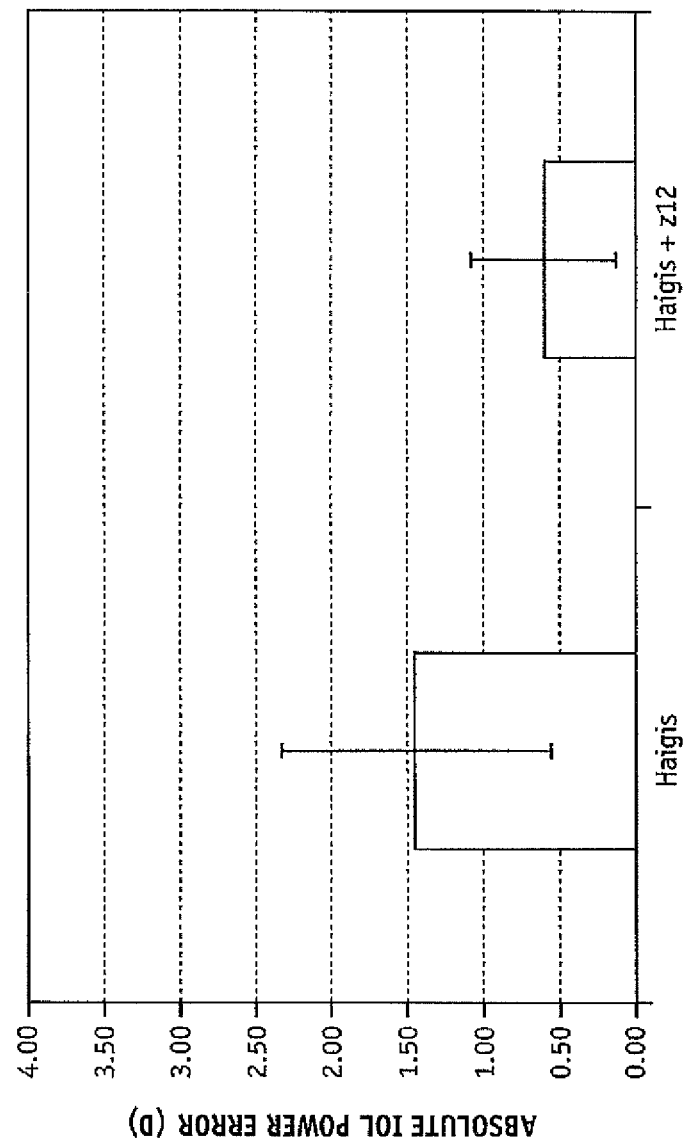
FIG. 19 shows the absolute IOL power prediction error both for the Haigis formula and the Haigis considering corneal spherical aberration for postlasik patients.

By way of additional non-limiting example, FIGS. 18 and 19 illustrate a comparison of the error of the predicted IOL power, for the referenced 29 non-average patients, for the Haigis and Haigis+z12 formulae. As shown, the inclusion of the adjustment for the SA substantially decreases the error in the predicted IOL power. More particularly, the Haigis+z12 formula indicated at step 170 of method 101 is:

$$P = 1.10511 + 0.986052*Haigis + 3.792270*z12. \quad \text{[EQUATION 6]}$$

Figure 20:
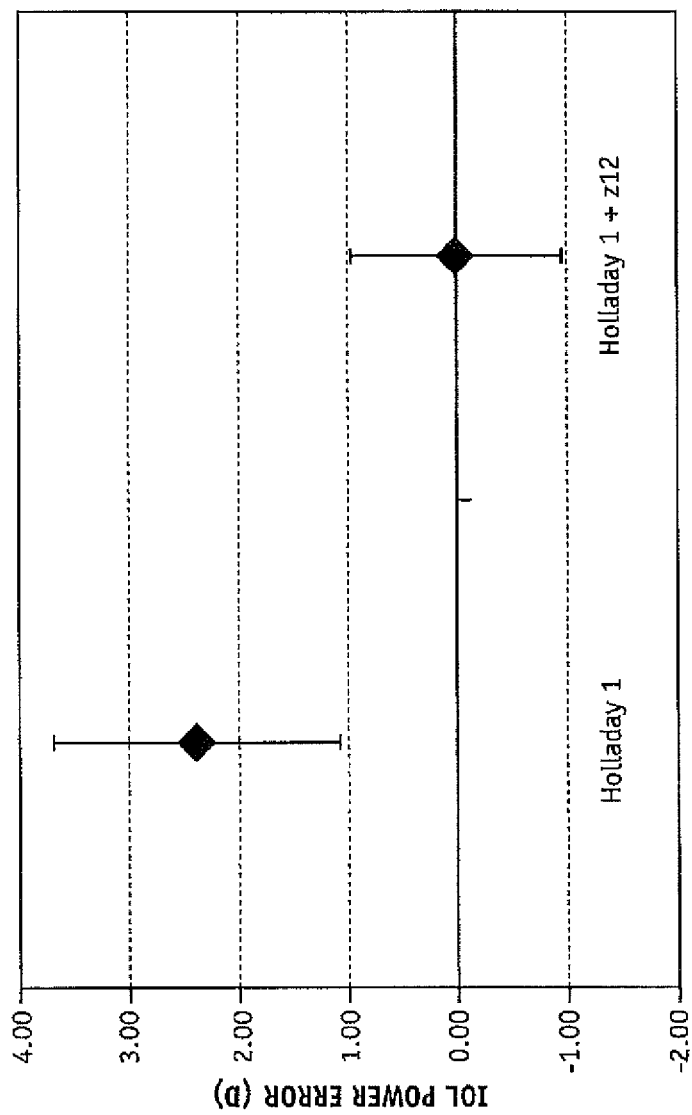
FIG. 20 shows the IOL power prediction error both for the Holladay1 formula and the Holladay1 considering corneal spherical aberration for postlasik patients.
Figure 21:
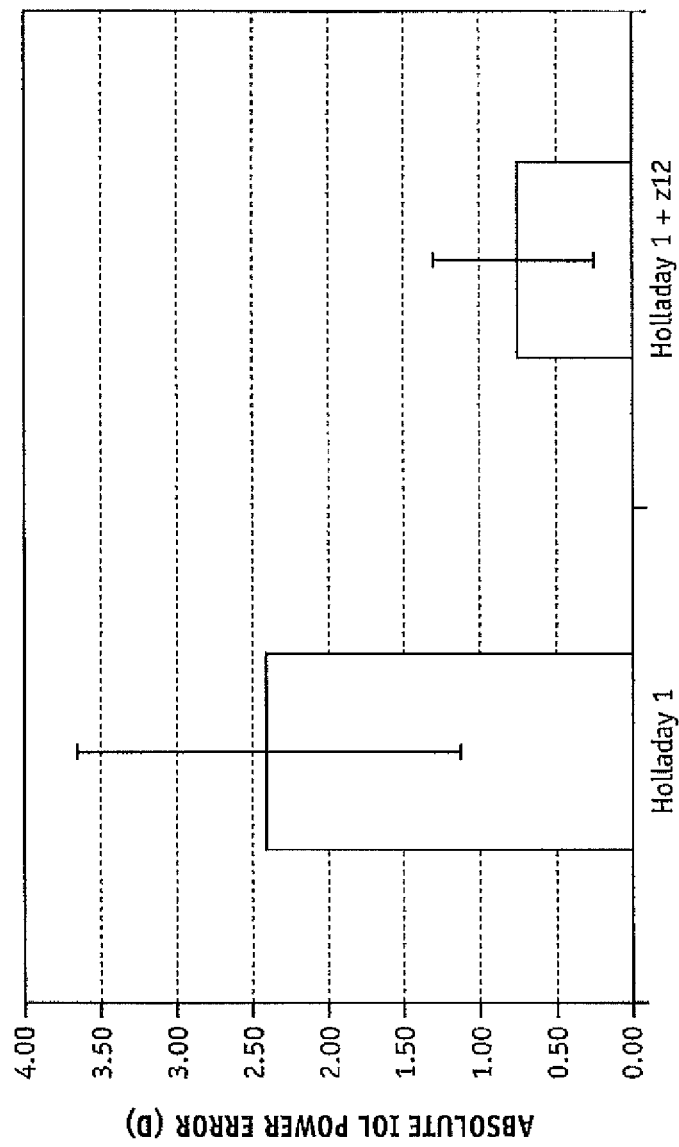
FIG. 21 shows the absolute IOL power prediction error both for the Holladay1 formula and the Holladay1 considering corneal spherical aberration for postlasik patients.

Yet further, FIGS. 20 and 21 illustrate a comparison of the error of the predicted IOL power, for the referenced 29 non-average patients, for the Holladay 1 and Holladay 1+z12 formulae. As shown, the inclusion of the adjustment for the SA substantially decreases the error in the predicted IOL power. More particularly, the Holladay 1+z12 formula indicated at step 170 of method 101 is:

$$P = 2.787859 + 0.888706*Holladay + 9.695131*z12. \quad \text{[EQUATION 7]}$$

For each of the aforementioned regressions, the effect of the modification for SA is statistically significant. Further, those skilled in the art will appreciate that the constants employed in EQUATIONS 4-7 are exemplary only, and thus may be modified yet still fall within the scope of the present invention. Thereby, modification to the exemplary constants respectively provided for z12 may be necessary.

In addition, method 100 was applied and a SRK modified+z12 formula was obtained at step 170, that is:

$$P = 140.8232 - 2.651*AXL - 1.3102*K + 4.767704*z12. \quad \text{[EQUATION 8]}$$

P represents the IOL power to implant. AXL represents the axial length measured prior to the surgery. K represents the corneal power also measured in the cataract preoperative stage. z12 represents the aforementioned corneal spherical aberration.

As referenced above, the Double K method with the Wang, Koch, Maloney correction or the Haigis L formula are manners of assessing IOL power for postlasik patients that are frequently employed in the current art.

Figure 22:
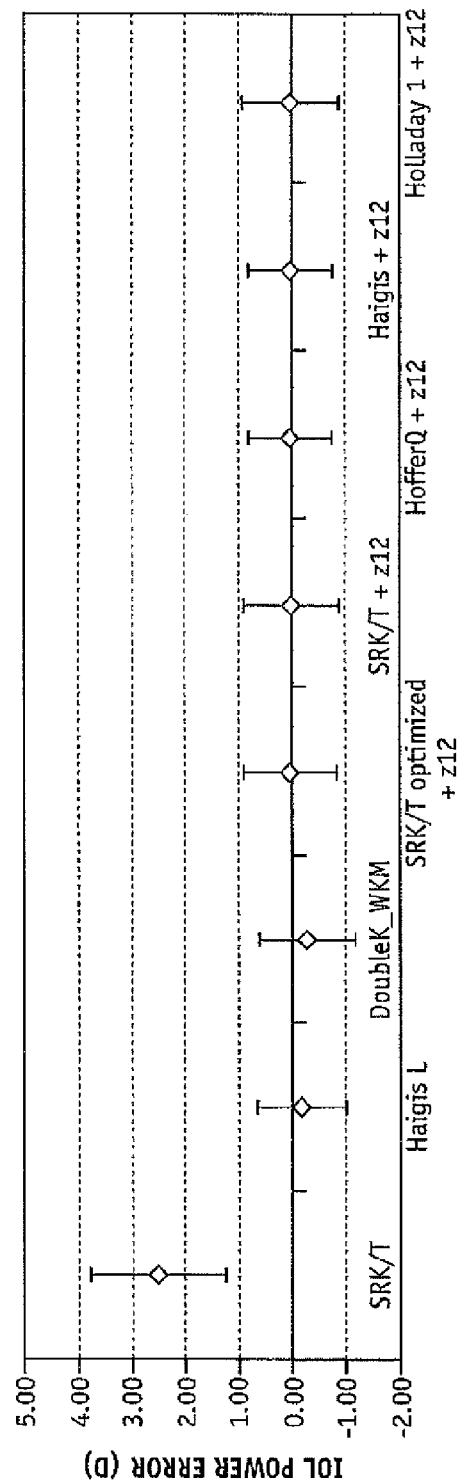
FIG. 22 shows the IOL power prediction error for different paraxial formulas considering corneal spherical aberration in comparison with the current state of art for postlasik patients.
Figure 23:
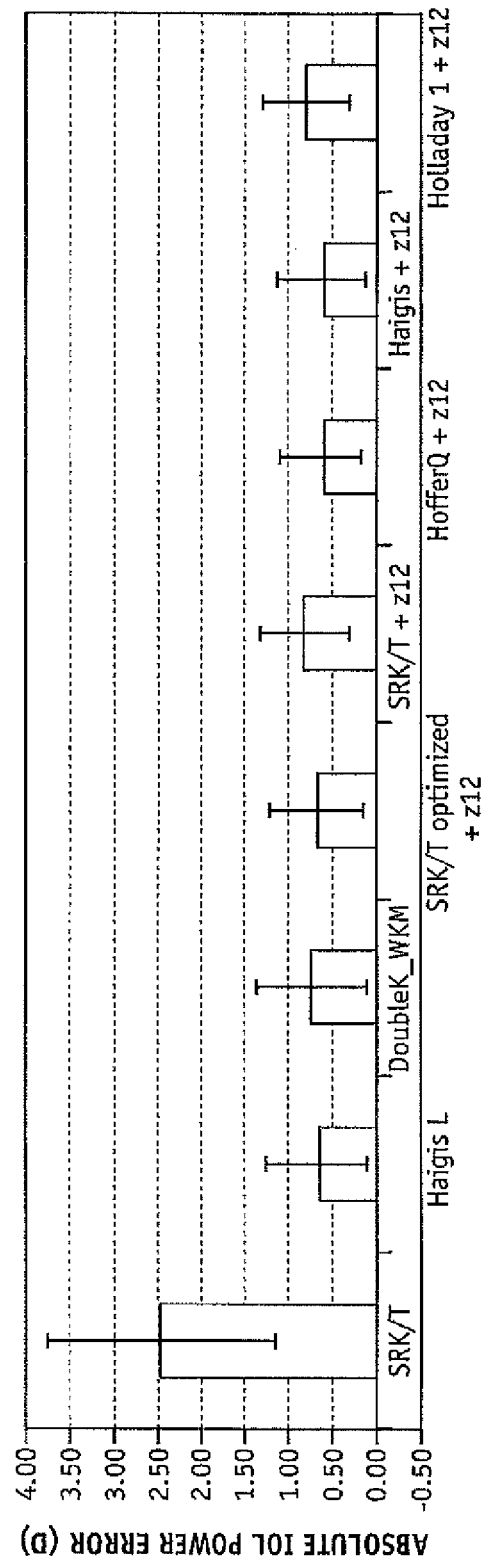
FIG. 23 shows the absolute IOL power prediction error for different paraxial formulas considering corneal spherical aberration in comparison with the current state of art for postlasik patients.

FIGS. 22-23 graphically illustrate the improvement in the required value minus the predicted value over the current state of the art, represented by the double K method with the Wang, Koch and Maloney (DoubleK_WKM) correction as well as the HagisL formula, provided by the present invention, particularly for the HofferQ+z12 and Haigis+z12 approaches. More particularly, Table 1 illustrates that the HofferQ+z12 and Haigis+z12 retrieved less error, less absolute error, and had an improved standard deviation as compared to the current state of art.

TABLE 1

|  | error | desvest | abs(error) | desvest |
|---|---|---|---|---|
| Haigis L | −0.22 | 0.86 | 0.66 | 0.58 |
| DoubleK_LW | −0.33 | 0.92 | 0.73 | 0.64 |
| SRK optimized + z12 | 0.00 | 0.88 | 0.68 | 0.55 |
| SRK/T + z12 | 0.00 | 0.97 | 0.81 | 0.50 |
| HofferQ + z12 | 0.00 | 0.79 | 0.62 | 0.48 |
| Haigis + z12 | 0.00 | 0.80 | 0.61 | 0.50 |
| Holladay1 + z12 | 0.00 | 0.95 | 0.79 | 0.51 |

Figure 24:
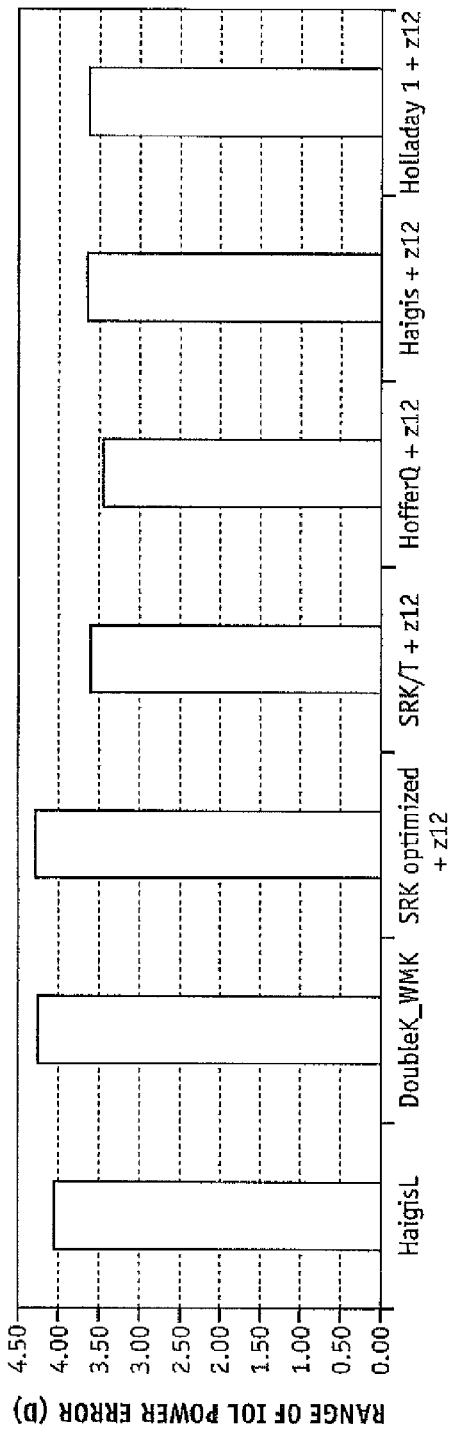
FIG. 24 shows the maximum range of IOL power prediction error for different paraxial formulas considering corneal spherical aberration in comparison with the current state of art for postlasik patients.

FIG. 24 shows the maximum range of error, defined as the most positive error minus the most negative error retrieved by each of the formulas for those patients included in the study. It discloses that, especially for those formulas retrieved by method 101, the range of error is reduced between 0.4 and 0.8D, thus making the calculated IOL power much more predictable. In the case of the SRK optimized+z12, the range of error is similar to those formulas that represent the current state of art.

Figure 25:
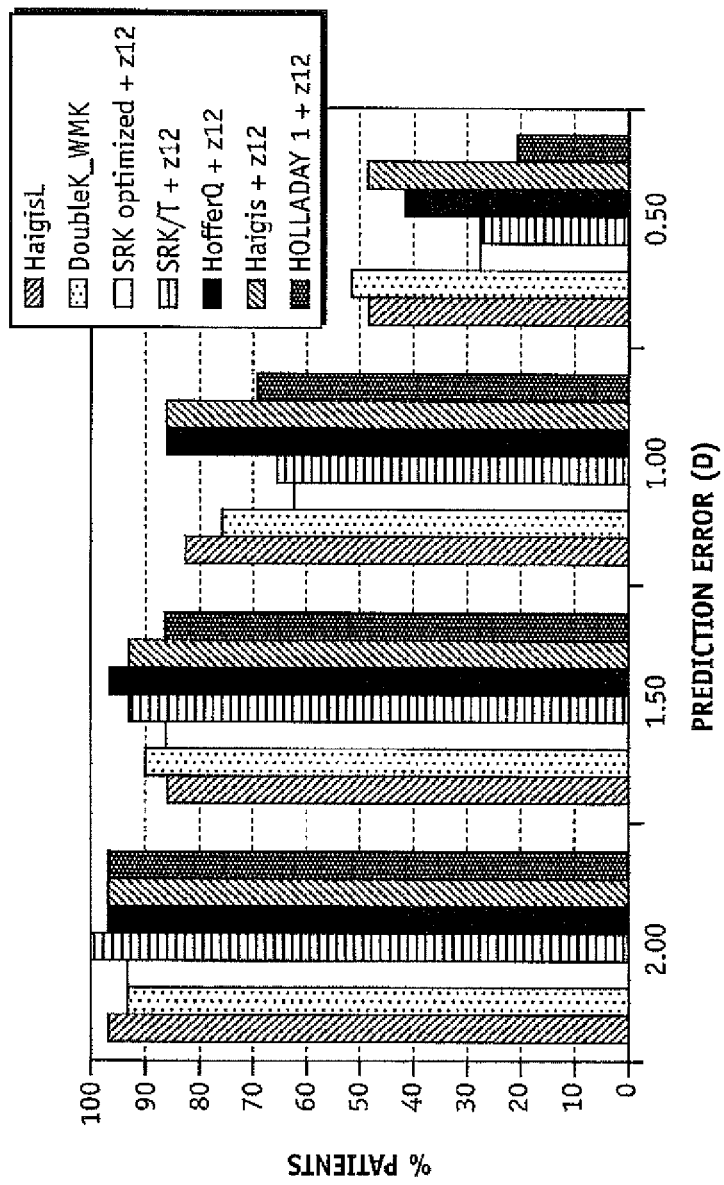
FIG. 25 shows the absolute IOL power prediction error in different ranges for different paraxial formulas considering corneal spherical aberration in comparison with the current state of art for postlasik patients.

In FIG. 25 the percentage of patients with different absolute prediction errors is shown for the different formulas. 86% of the patients are inside 1D with Haigis+z12 or HofferQ+z12. 97% and 93% respectively can be calculated with accuracy better than 1.5D, thus illustrating higher accuracy for these formulas incorporating corneal spherical aberration than those representing the current state of art for IOL power calculations in postlasik patients.

Figure 26:
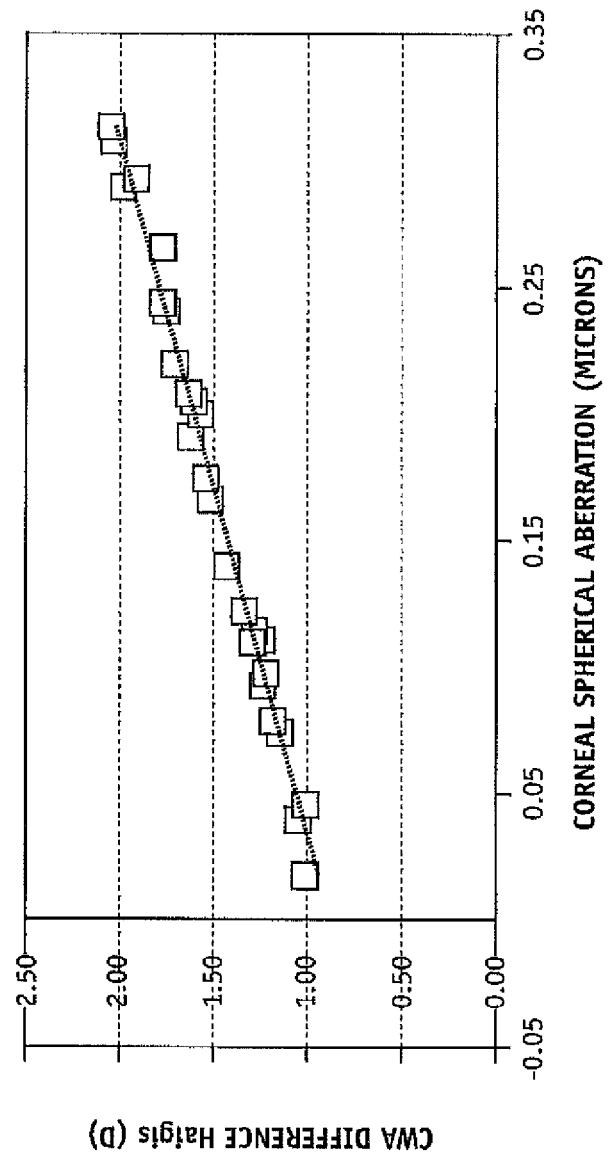
FIG. 26 illustrates difference between IOL power calculation for the Haigis formula considering spherical aberration and the Haigis paraxial formula versus corneal spherical aberration calculated at 4 mm pupil for postlasik patients.
Figure 27:
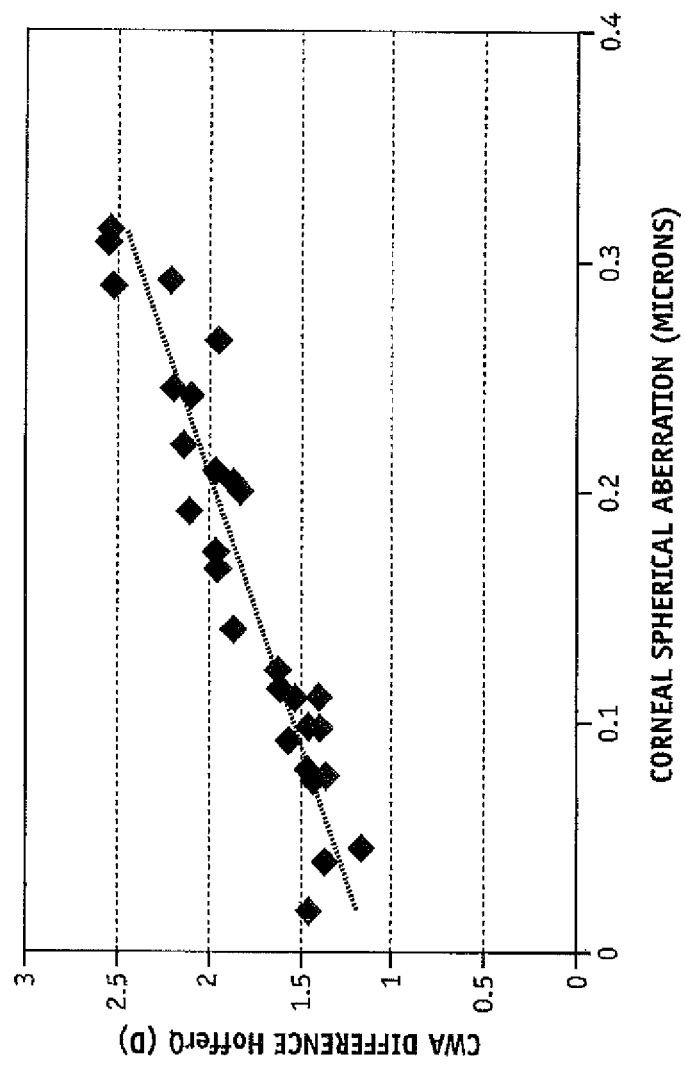
FIG. 27 illustrates difference between IOL power calculation for the HofferQ formula considering spherical aberration and the HofferQ paraxial formula versus corneal spherical aberration calculated at 4 mm pupil for postlasik patients.

FIG. 26 illustrates the IOL power prediction difference defined as Haigis+z12 formula result minus the regular Haigis formula result for each patient ("CWA difference Haigis"), which in the exemplary embodiments is by at least 1 Diopter. This difference increases with corneal spherical aberration up to 2D. Similarly, FIG. 27 discloses the same behavior with respect to the HofferQ+z12 and HofferQ formulas, reaching in this case up to 2.5D.

Thus, the present invention takes into consideration SA using simple linear regression to modify existing IOL power regression formulae to allow those existing IOL power regression formulae to be used for non-average patients, such as postlasik patients. Of course, the improvement in predictive accuracy depends on the base classical regression formula used, at least in that the modified SRK/T+z12 and Holladay 1+z12 provide results comparable with the current state of the art, and the HofferQ+z12 and Haigis+z12 modified formulae provide an appreciably improved predictive outcome as compared to the current state of the art.

It is important to be note that, just as the A constant is changed depending on the IOL model, the D constant may also need to be modified depending on the IOL model.

Of course, those skilled in the pertinent arts will appreciate, in light of the discussion herein, that the customized regression of the present invention developed at step 170 of methods 100 or 101 may include terms accounting for variables other than, or in addition to, the aforementioned accounting for SA. Such terms may account for other variables such as, for example, ACD, other aberrations, or the like, through the use of known conversions of those variables for use in a regression calculation or with a mathematical treatment other than a linear relationship.

Figure 28:
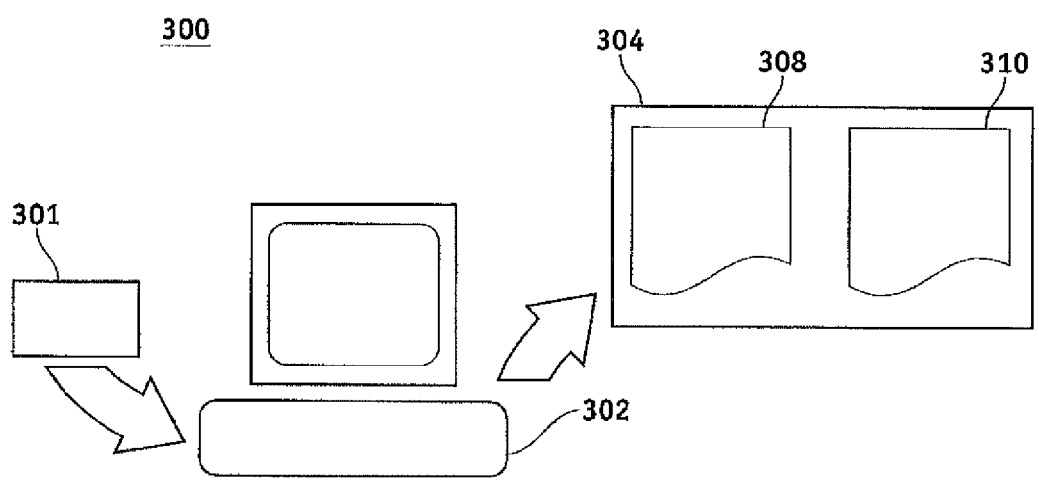
FIG. 28 is a block diagram illustrating the implementation of the present invention in a clinical system.

FIG. 28 is a block diagram illustrating the implementation of the present invention in a clinical system 300 comprised of one or more apparatuses that of capable of assessing the eye's biometry and of performing the calculations and comparisons set forth in methods 100 and 101, as well as the IOL power prediction set in procedure 200. The system 300 may include a biometric reader 301, a processor 302, and a computer readable memory 304 coupled to the processor 302. The computer readable memory 304 includes therein an array of ordered values 308 and sequences of instructions 310 which, when executed by the processor 302, cause the processor 302 to select an implantable IOL configured for implantation into the eye of the subject presenting the biometric readings to biometric reader 301, which feed the system with all the biometric data needed for the programmed calculation. The array of ordered values 308 may comprise data used or obtained from method 100 or 101 or other methods consistent with embodiments of the invention. For example, the array of ordered values 308 may comprise one or more desired refractive outcomes, parameters of an eye model based on one or more characteristics of at least one eye, and data related to an IOL or set of IOLs such as a power, an aspheric profile, and/or a lens plane.

The sequence of instructions 310 may include one or more steps of methods 100 and 101 or other methods consistent with embodiments of the invention. In some embodiments, the sequence of instructions 310 includes applying the custom regression of procedure 200, performing one or more calculations to determine the optimum IOL to implant achieving the desired outcome based on the formula obtained at the step 170.

The processor 302 may be embodied in a general purpose desktop or laptop computer, and/or may comprise hardware associated with biometric reader 301 specifically for selecting an IOL for placement into the eye of the subject. In certain embodiments, the system 300 may be configured to be electronically coupled to another device, such as one or more instruments for obtaining measurements of an eye or a plurality of eyes. From these measurements, methods 100 and/or 101 can be used to update the formula obtained at step 170. Alternatively, the system 300 may be embodied in a handheld device that may be adapted to be electronically and/or wirelessly coupled to one or more other devices.

Those of ordinary skill in the art may recognize that many modifications and variations of the present invention may be implemented without departing from the spirit or scope of the invention. Thus, it is intended that the present invention covers the modifications and variations of this invention provided they come within the scope of the discussion herein and any appended claims, and any equivalents thereto.

What is claimed is:

1. A system for predicting optical power for an intraocular lens, comprising:
a first device configured to measure at least one biometric parameter of an eye;
a second device configured to obtain a corneal spherical aberration of the eye according to the at least one biometric parameter;
at least one computing processor configured to apply a modified regression to the at least one biometric parameter and the corneal spherical aberration to output a prediction of an optical power for an intraocular lens to obtain a desired postoperative condition, wherein the modified regression is of the form:

optical power=Regression+constant0*(corneal spherical aberration)

or optical power=constant1*(biometric parameter)+constant0*(corneal spherical aberration);

wherein constant1 and constant0 comprise an empirically derived factor across other eyes, and wherein Regression comprises a classical regression.

2. The system of claim 1, further comprising a feedback input to the at least one computing processor for modifying the modified regression in accordance with the determination of the optical power.

3. The system of claim 1, wherein the at least one biometric parameter comprises at least one of axial length, anterior chamber depth and corneal power.

4. The system of claim 1, wherein the desired postoperative condition comprises a postoperative refraction.

5. The system of claim 1, wherein Regression comprises one selected from at least Hoffer Q regression, Haigis regression, Holladay1 regression, Holladay2 regression, and SRK/T regression.

6. The system of claim 1, wherein the system comprises a corneal topographer and the second device obtains the corneal spherical aberration of the eye by the corneal topographer.

7. The system of claim 6, wherein the second device comprises a computing device including a ray tracing software.

8. The system of claim 1, wherein the first device comprises a biometric reader.

* * * * *